(12) United States Patent
Beyer

(10) Patent No.: US 10,888,356 B2
(45) Date of Patent: Jan. 12, 2021

(54) ORTHOPEDIC IMPLANT KIT

(71) Applicant: Neo Medical SA, La Villette (CH)

(72) Inventor: Morten Beyer, Rød kærsbro (DK)

(73) Assignee: Neo Medical S.A., La Villette (CH)

( * ) Notice: Subject to any disclaimer, the term of this patent is extended or adjusted under 35 U.S.C. 154(b) by 41 days.

(21) Appl. No.: 15/939,338

(22) Filed: Mar. 29, 2018

(65) Prior Publication Data

US 2018/0214186 A1 Aug. 2, 2018

Related U.S. Application Data

(63) Continuation of application No. 14/890,631, filed as application No. PCT/IB2014/060979 on Apr. 24, 2014, now Pat. No. 10,058,355.

(30) Foreign Application Priority Data

May 13, 2013 (WO) .................. PCT/IB2013/053892

(51) Int. Cl.
    *A61B 17/70* (2006.01)
    *A61B 17/88* (2006.01)

(52) U.S. Cl.
    CPC ...... *A61B 17/7037* (2013.01); *A61B 17/7002* (2013.01); *A61B 17/708* (2013.01); *A61B 17/7032* (2013.01); *A61B 17/7038* (2013.01); *A61B 17/7085* (2013.01); *A61B 17/7086* (2013.01); *A61B 17/7091* (2013.01); *A61B 17/8875* (2013.01)

(58) Field of Classification Search
    CPC .............. A61B 17/708; A61B 17/7077; A61B 17/7083; A61B 17/7085; A61B 17/7086; A61B 17/7088; A61B 17/7089; A61B 17/7091
    See application file for complete search history.

(56) References Cited

U.S. PATENT DOCUMENTS

| | | |
|---|---|---|
| 3,650,393 A | 3/1972 | Reiss et al. |
| 4,834,757 A | 5/1989 | Brantigan |
| 5,669,909 A | 9/1997 | Zdeblick et al. |
| 5,728,098 A | 3/1998 | Sherman et al. |
| 5,797,918 A | 8/1998 | McGuire et al. |
| 5,913,860 A | 6/1999 | Scholl |
| 6,113,601 A | 9/2000 | Tatar |

(Continued)

FOREIGN PATENT DOCUMENTS

| | | |
|---|---|---|
| CN | 102026584 | 4/2011 |
| CN | 202446242 | 9/2012 |

(Continued)

OTHER PUBLICATIONS

Japanese Office Action issued by the Japanese Patent Office in the counterpart Japanese Application No. 2016-513463 of dated Aug. 14, 2018 and English translation thereof.

(Continued)

*Primary Examiner* — Lynnsy M Summitt
(74) *Attorney, Agent, or Firm* — Andre Roland S.A.; Nikolaus Schibli

(57) ABSTRACT

An orthopedic implant kit comprising a lockable poly-axial screw, a tissue dilatation sleeve, a screw driver, a screw extender, a rod, rod-reduction device, a set screw driver, a torque limiting device and a screw releasing device.

18 Claims, 24 Drawing Sheets

(56) References Cited

U.S. PATENT DOCUMENTS

| | | |
|---|---|---|
| 6,368,321 B1 | 4/2002 | Jackson |
| 6,371,968 B1 | 4/2002 | Kogasaka et al. |
| 6,423,064 B1 | 7/2002 | Kluger |
| 6,644,087 B1 | 11/2003 | Ralph et al. |
| 6,716,214 B1 | 4/2004 | Jackson |
| 6,743,231 B1 | 6/2004 | Gray et al. |
| 7,066,937 B2 | 6/2006 | Shluzas |
| 7,160,300 B2 | 1/2007 | Jackson |
| 7,179,225 B2 | 2/2007 | Sum et al. |
| 7,250,052 B2 | 7/2007 | Landry et al. |
| 7,491,168 B2 | 2/2009 | Raymond |
| 7,520,879 B2 | 4/2009 | Justis et al. |
| 7,527,638 B2 | 5/2009 | Anderson et al. |
| 7,588,575 B2 | 9/2009 | Colleran et al. |
| 7,604,655 B2 | 10/2009 | Warnick |
| 7,651,502 B2 * | 1/2010 | Jackson ............ A61B 17/7086 606/99 |
| 7,666,189 B2 * | 2/2010 | Gerber ............ A61B 17/7074 606/104 |
| 7,691,129 B2 | 4/2010 | Felix |
| 7,691,132 B2 | 4/2010 | Landry et al. |
| 7,744,629 B2 * | 6/2010 | Hestad ............ A61B 17/025 411/452 |
| 7,749,232 B2 | 7/2010 | Salerni |
| 7,811,288 B2 | 10/2010 | Jones et al. |
| 7,842,044 B2 | 11/2010 | Runco et al. |
| 7,862,587 B2 * | 1/2011 | Jackson ............ A61B 17/861 606/246 |
| 7,892,238 B2 | 2/2011 | DiPoto et al. |
| 7,892,259 B2 | 2/2011 | Biedermann et al. |
| 7,922,725 B2 * | 4/2011 | Darst Rice ........ A61B 17/8869 606/86 A |
| 7,931,673 B2 * | 4/2011 | Hestad ............ A61B 17/7085 606/246 |
| 7,951,172 B2 | 5/2011 | Chao et al. |
| 7,967,821 B2 | 6/2011 | Sicvol et al. |
| 8,016,832 B2 * | 9/2011 | Vonwiller .......... A61B 17/7032 606/86 A |
| 8,016,862 B2 | 9/2011 | Felix et al. |
| 8,034,086 B2 | 10/2011 | Iott et al. |
| 8,052,724 B2 | 11/2011 | Jackson |
| 8,088,163 B1 | 1/2012 | Kleiner |
| 8,114,085 B2 | 2/2012 | Von Jako |
| 8,128,667 B2 | 3/2012 | Jackson |
| 8,137,356 B2 * | 3/2012 | Hestad ............ A61B 17/708 606/279 |
| 8,152,810 B2 | 4/2012 | Jackson |
| 8,167,911 B2 | 5/2012 | Shluzas et al. |
| 8,197,519 B2 | 6/2012 | Schlaepfer et al. |
| 8,246,665 B2 | 8/2012 | Butler et al. |
| 8,262,662 B2 | 9/2012 | Beardsley et al. |
| 8,262,704 B2 * | 9/2012 | Matthis ............ A61B 17/7032 606/264 |
| 8,317,796 B2 * | 11/2012 | Stihl ................ A61B 17/7091 606/279 |
| 8,366,747 B2 | 2/2013 | Shluzas |
| 8,372,121 B2 | 2/2013 | Capote et al. |
| 8,382,805 B2 | 2/2013 | Wang et al. |
| 8,394,109 B2 * | 3/2013 | Hutton ............ A61B 17/7032 606/105 |
| 8,465,546 B2 | 6/2013 | Jodaitis et al. |
| 8,469,960 B2 | 6/2013 | Hutton et al. |
| 8,562,652 B2 | 10/2013 | Biedermann et al. |
| 8,603,094 B2 * | 12/2013 | Walker ............ A61B 17/708 606/246 |
| 8,603,145 B2 | 12/2013 | Forton et al. |
| 8,608,746 B2 * | 12/2013 | Kolb ................ A61B 17/7076 606/86 A |
| 8,617,218 B2 * | 12/2013 | Justis ............... A61B 17/7085 606/278 |
| 8,636,783 B2 | 1/2014 | Crall et al. |
| 8,870,878 B2 | 10/2014 | Gorek |
| 9,050,139 B2 | 6/2015 | Jackson |
| 9,066,758 B2 * | 6/2015 | Justis ............... A61B 17/7082 |
| 9,066,761 B2 * | 6/2015 | McBride ........... A61B 17/7085 |
| 9,101,401 B2 | 8/2015 | Dalton |
| 9,138,261 B2 | 9/2015 | Di Lauro et al. |
| 9,204,909 B2 | 12/2015 | Rezach |
| 9,211,143 B2 | 12/2015 | Barry |
| 9,211,149 B2 | 12/2015 | Hoefer et al. |
| 9,326,798 B2 * | 5/2016 | Kolb ................ A61B 17/7076 |
| 9,408,649 B2 | 8/2016 | Felix et al. |
| 9,492,209 B2 * | 11/2016 | Biedermann ...... A61B 17/7085 |
| 9,526,537 B2 * | 12/2016 | Meyer .............. A61B 17/7086 |
| 9,585,702 B2 | 3/2017 | Hutton et al. |
| 9,655,653 B2 * | 5/2017 | Lindner ............ A61B 17/7032 |
| 9,707,019 B2 | 7/2017 | Miller et al. |
| 9,924,982 B2 * | 3/2018 | Jackson ............ A61B 17/7085 |
| 9,962,197 B2 * | 5/2018 | Dandaniopoulos .. A61B 17/708 |
| 9,968,378 B1 | 5/2018 | Johnson et al. |
| 2004/0144149 A1 | 7/2004 | Strippgen et al. |
| 2005/0131408 A1 * | 6/2005 | Sicvol ............... A61B 17/7032 606/86 A |
| 2005/0192570 A1 | 9/2005 | Jackson |
| 2005/0192579 A1 * | 9/2005 | Jackson ............ A61B 17/7085 606/914 |
| 2005/0240197 A1 | 10/2005 | Kmiec, Jr. |
| 2006/0036244 A1 | 2/2006 | Spitler et al. |
| 2006/0089644 A1 | 4/2006 | Lee et al. |
| 2006/0111712 A1 | 5/2006 | Jackson |
| 2006/0111715 A1 * | 5/2006 | Jackson ............ A61B 17/861 128/897 |
| 2006/0217719 A1 | 9/2006 | Albert et al. |
| 2006/0241599 A1 | 10/2006 | Konieczynski et al. |
| 2007/0078460 A1 | 4/2007 | Frigg et al. |
| 2007/0106123 A1 | 5/2007 | Gorek et al. |
| 2007/0233091 A1 | 10/2007 | Naifeh et al. |
| 2007/0239159 A1 | 10/2007 | Altarac et al. |
| 2007/0270866 A1 | 11/2007 | Von Jako |
| 2008/0039839 A1 | 2/2008 | Songer et al. |
| 2008/0119852 A1 | 5/2008 | Dalton et al. |
| 2008/0147129 A1 | 6/2008 | Biedermann et al. |
| 2008/0154279 A1 | 6/2008 | Schumacher et al. |
| 2008/0243189 A1 | 10/2008 | Purcell et al. |
| 2008/0262318 A1 | 10/2008 | Gorek et al. |
| 2008/0294203 A1 | 11/2008 | Kovach et al. |
| 2009/0171391 A1 | 7/2009 | Hutton et al. |
| 2009/0204159 A1 | 8/2009 | Justis et al. |
| 2009/0221879 A1 | 9/2009 | Gorek |
| 2009/0222045 A1 | 9/2009 | Gorek |
| 2010/0152785 A1 | 6/2010 | Forton |
| 2010/0312103 A1 | 12/2010 | Gorek et al. |
| 2011/0040328 A1 | 2/2011 | Miller et al. |
| 2011/0106179 A1 | 5/2011 | Prevost et al. |
| 2011/0166606 A1 * | 7/2011 | Stihl ................ A61B 17/7086 606/279 |
| 2011/0172718 A1 | 7/2011 | Felix et al. |
| 2011/0245883 A1 | 10/2011 | Dall |
| 2011/0263945 A1 | 10/2011 | Peterson et al. |
| 2011/0313460 A1 | 12/2011 | McLean et al. |
| 2011/0319896 A1 | 12/2011 | Papenfuss et al. |
| 2012/0031792 A1 | 2/2012 | Petit et al. |
| 2012/0186411 A1 | 7/2012 | Lodahi et al. |
| 2013/0012999 A1 | 1/2013 | Petit |
| 2013/0023941 A1 | 1/2013 | Jackson et al. |
| 2013/0096624 A1 | 4/2013 | Di Lauro et al. |
| 2014/0031828 A1 | 1/2014 | Patel et al. |
| 2014/0052187 A1 * | 2/2014 | McBride ........... A61B 17/708 606/264 |
| 2014/0100613 A1 * | 4/2014 | Iott .................. A61B 17/7074 606/279 |
| 2014/0171955 A1 | 6/2014 | Smith |
| 2015/0066042 A1 * | 3/2015 | Cummins .......... A61B 17/7037 606/104 |
| 2015/0265322 A1 * | 9/2015 | Jackson ............ A61B 17/7085 606/86 A |
| 2015/0351810 A1 * | 12/2015 | Lindner ............ A61B 17/7032 606/278 |
| 2016/0166304 A1 | 6/2016 | Stad et al. |
| 2016/0287294 A1 | 10/2016 | Kubo et al. |
| 2016/0346026 A1 | 12/2016 | Bootwala et al. |
| 2016/0374825 A1 | 12/2016 | Kleiner |

(56) References Cited

U.S. PATENT DOCUMENTS

| | | | | |
|---|---|---|---|---|
| 2017/0095272 A1* | 4/2017 | Hutton | ............... | A61B 17/7032 |
| 2017/0143384 A1* | 5/2017 | Hutton | ............... | A61B 17/7032 |
| 2017/0181775 A1* | 6/2017 | Jackson | ............. | A61B 17/7091 |
| 2017/0189082 A1 | 7/2017 | Petit | | |
| 2017/0348037 A1 | 12/2017 | Sexson et al. | | |

FOREIGN PATENT DOCUMENTS

| | | |
|---|---|---|
| CN | 202497225 U | 10/2012 |
| CN | 203777040 | 8/2014 |
| CN | 1005662662 | 6/2016 |
| EP | 1994902 | 11/2008 |
| EP | 2283787 | 2/2011 |
| EP | 2522287 | 11/2012 |
| JP | 2007283101 | 11/2007 |
| JP | 2011500267 | 1/2011 |
| JP | 2012507316 | 3/2012 |
| JP | 2013515580 | 5/2013 |
| TW | M273326 U | 8/2005 |
| WO | WO 9819616 | 5/1998 |
| WO | WO 2006045089 | 4/2006 |
| WO | WO 2006091863 | 8/2006 |
| WO | WO 2006/130179 | 12/2006 |
| WO | WO 2007092870 | 8/2007 |
| WO | WO 2007117366 | 10/2007 |
| WO | WO 2008097974 | 8/2008 |
| WO | 2009/055026 A1 | 4/2009 |
| WO | WO 2009055034 | 4/2009 |
| WO | WO 2009/114422 | 9/2009 |
| WO | WO 2010052462 | 5/2010 |
| WO | WO 2011080426 | 7/2011 |

OTHER PUBLICATIONS

Second Office Action issued from the European Patent Office (EPO) as an Article 94(3) EPC Communication of Aug. 29, 2018 in the counterpart application with the Serial No. 14 734 227.3.
Third Party Observation filed on Jun. 26, 2019 against EPO Patent Application No. EP20100810769 (Publication No. EP2519180, corresponding to U.S. Pat. Pub. No. 2017/0189082).
First Office Action dated May 7, 2017 for the State Intellectual Property Office of China (SIPA) for the counterpart application with the Serial No. 201480027310.0.
International Search Report dated Nov. 25, 2014 in International Application No.PCTIIB2014/060979, 5 pages.
Japanese Office Action issued by the Japanese Patent Office in the counterpart Japanese Application No. 2016-513463 dated Feb. 6, 2018, 9 pages + English translation.
Second Office Action dated Feb. 5, 2018 for the State Intellectual Property Office of China (SIPA) for the counterpart application with the Serial No. 201480027310.0.
Notification of granting patent right of Jun. 6, 2019 for the State Intellectual Property Office of China (SIPA) for the counterpart application with the Serial No. 201480027310.0.
Third Office Action issued from the European Patent Office (EPO) as an Article 94(3) EPC Communication of May 3, 2019 for Serial No. 14 734 227.3.
Office Action dated Aug. 20, 2019 from the Japanese Patent Office ("JPO") for counterpart application with Application Serial No. JP2018-199618 with English Translation.
Opposition against European Patent No. 2 526 888 (EPO Application No. 12 177 688.4) dated Apr. 21, 2018, EP counterpart of U.S. Pat. Pub. No. 2017/0189082.
Indian first Office Action dated Sep. 10, 2020 for Application IN 10594/DELNP/2015.
Japanese Appeal Decision dated Aug. 18, 2020 for Application No. 2016-513463 + translation EN.
Opposition against European U.S. Pat. No. 2 526 888, Oppnent Response of dated Mar. 31, 2020.

* cited by examiner

ORTHOPEDIC IMPLANT KIT

CROSS-REFERENCE TO RELATED APPLICATIONS

The present application is a continuation application of U.S. Ser. No. 14/890,631 that was filed on Nov. 12, 2015, now U.S. Pat. No. 10,058,355, which is a U.S. national stage application of International patent application PCT/IB2014/060979, filed on Apr. 24, 2014, which designated the United States, and claims foreign priority to International patent application PCT/IB2013/053892, filed on May 13, 2013, the entire contents of all three documents being herewith incorporated by reference.

FIELD OF INVENTION

The present invention relates to orthopedics and more precisely to orthopedic items such as pedicle screws, rods and spine cages. The invention also relates to instruments which are used for manipulating those items.

BACKGROUND

US 2013/0012999 discloses an orthopedic implant kit comprising several items, in particular a pedicle screw fixed to a mounting tube made of two half-shells which can be easily disassembled.

Pedicle screws of the prior art can be divided in two main groups:

Mono-axial screws: The direction of the screw main axis is fixed with respect the screw head;

Poly-axial screws: The orientation of the screw main axis can be freely modified with respect to the screw head.

When implanting a pedicle screw into a bone several steps are needed. For almost each of those steps a dedicated instrument is used.

GENERAL DESCRIPTION OF THE INVENTION

An objective of the present invention is to reduce the number of items which are required for manipulating and fixing an orthopedic implant (pedicle screw, nut, rod, etc . . . ).

Another objective is to reduce the number of instruments for manipulating those items.

Another objective is to facilitate the handling of the instruments.

Those objectives are met with the implant kit and the related items and instruments which are defined in the claims.

In a first embodiment the invention consists in an orthopedic implant kit comprising a lockable poly-axial screw, a tissue dilatation sleeve, a screw driver, a screw extender, a rod, rod-reduction means, a set screw driver, a torque limiting mechanism and a screw releasing instrument.

The lockable poly-axial orthopedic screw according to the invention comprises a head and a threaded portion which form two separate elements, fixed to each other but each element may be independently oriented along a specific direction. The threaded portion may, for instance, rotates around the screw head and may adopt several possible orientations. More precisely, the threaded portion may be oriented anywhere within a conical volume, the top of the cone corresponding to the contact point between the head and the threaded portion.

The screw furthermore comprises a locking element which, when activated, suppresses the relative movement between the threaded portion and the head. This configuration is named "mono-axial" because the threaded portion may be oriented along a single (fixed) axis with respect to the head.

According one embodiment the locking element is a clip having a U-shape. In this case the head and the threaded portion contains cavities which are adapted to receive the branches of the U-shape clip.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

In another embodiment the screw head contains at least one longitudinal relief, such as a groove or a ridge, which is dimensioned in a way as to receive a corresponding relief, such as a ridge or a groove, which is located within the distal end of a screw extender.

In another embodiment the screw comprises a concave seat located in the proximal end of the threaded portion and a corresponding convex shape located at the distal part of the screw head. This configuration reduces the screw length and increases the strength and the rigidity of the system.

The screw extender according to the invention comprises a hollow cylindrical body made of two half tubes separated by two opposite longitudinal slots having an open end towards the cylindrical body distal part, this later one being dimensioned to receive and hold a screw head. The cylindrical body furthermore comprises an internal threaded part.

According to one embodiment the cylindrical body is made of a single piece and the distal part is radially expandable by its own elasticity, in such a way as to allow an easy clipping and subsequent releasing of a screw head.

To facilitate its radial expansion, the screw extender may include expanding means, for instance an internal rotatable tube which, when rotated pushes away the two half tubes from each other.

In a preferred embodiment the internal part of the cylindrical body distal end contains at least one relief, such as a ridge or a groove, which is dimensioned to be received within the longitudinal relief of a screw head which includes a corresponding relief, as mentioned previously. With this configuration it hinders the distal part of the half tubes to separate from each other by its own elasticity thus making a very strong attachment between the screw extender and the screw head. An additional benefit is that the relative rotation between the screw head and the cylindrical body is avoided.

In a preferred embodiment a rod reduction instrument is located within the cylindrical body.

Advantageously the rod reduction instrument is essentially made of a shaft with a threaded distal part which is the counterpart of the cylindrical body internal threaded part. So when it is rotated within the cylindrical body the shaft may move along the cylindrical body main axis.

In another embodiment a set screw driver is (also or alternatively) located within said cylindrical body. In this case also, the set screw driver may also essentially be made of a shaft with a threaded distal part.

Advantageously the set screw driver comprises a torque limiting mechanism.

In one embodiment this mechanism includes a breakable pin and a thread free rotatable shaft. The pin is laterally crossing the rotatable shaft and its ends are fixed within the threaded rotatable shaft.

The threaded and the threaded free shafts are rotatably linked to each other but when a certain torque is reached the pin breaks and each shaft may freely rotates with respect to the other shaft.

In another embodiment a screw releasing instrument is (also or alternatively) located within said cylindrical body.

Advantageously the screw releasing instrument is essentially made of a shaft with a threaded distal part.

In a particularly interesting embodiment, the same shaft with a threaded distal part is used for the rod reduction instrument (and potential sponylolisthesis), the set screw driver and the screw releasing mechanism.

The tissue dilatation sleeve according to the invention comprises a flexible conical part which is adapted to be temporarily fixed to the distal part of an instrument such as a screw extender as defined in the previous claims.

In one embodiment the conical part is made of several longitudinal flexible blades having each a substantially triangular shape.

DETAILED DESCRIPTION OF THE INVENTION

The invention will be better understood in the following part of this document, with non-limiting examples illustrated by the following figures.

NUMERICAL REFERENCES USED IN THE FIGURES

Figure 1:
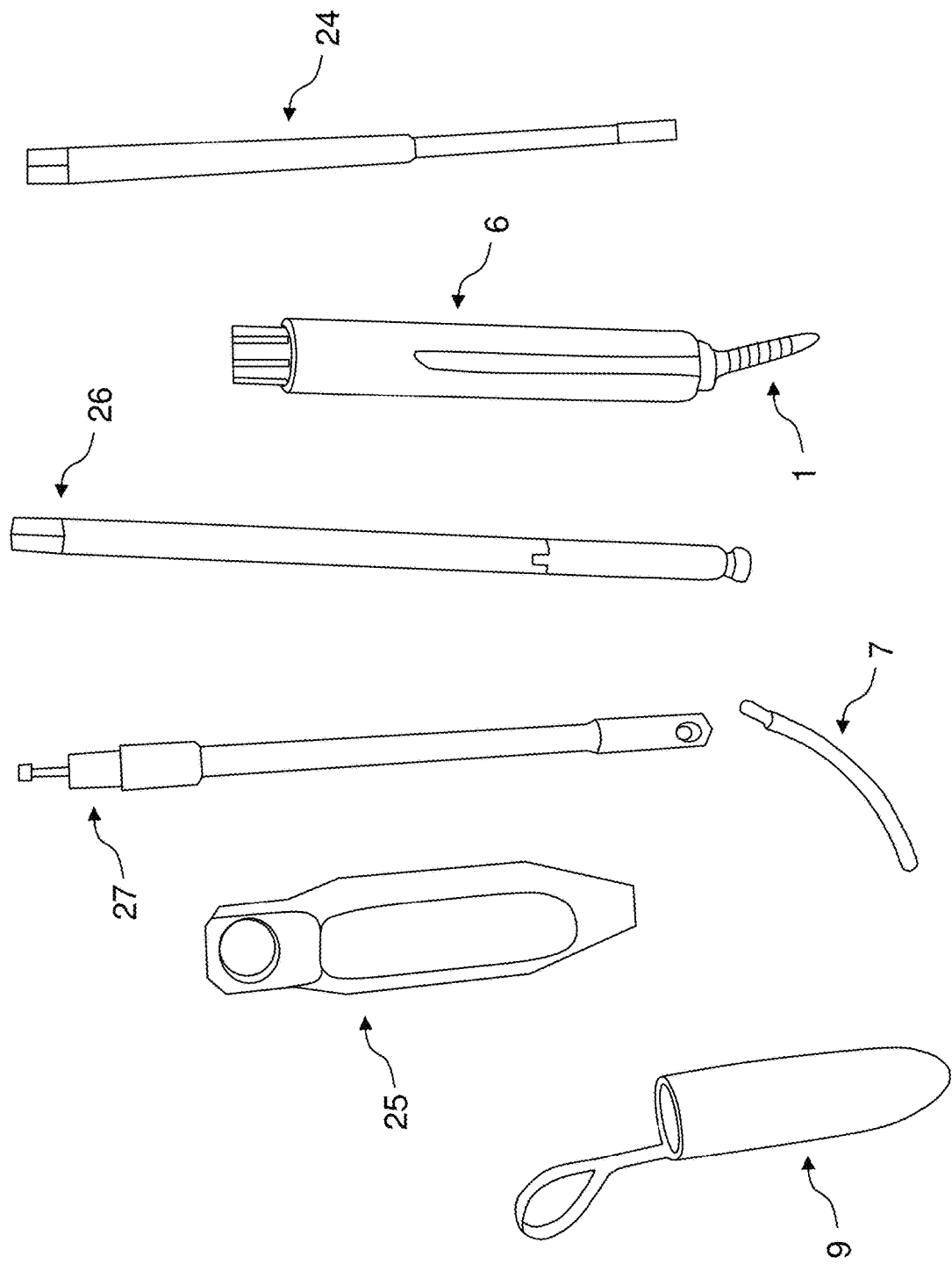
FIG. 1 shows an implant kit according to the invention

1. Pedicle screw
2. Head
3. Set screw
4. Threaded portion
5. Locking element
6. Screw extender
7. Rod
8. Multi-use instrument upper part
9. Tissue dilatation sleeve
10. Torque driver
11. Head passage
12. Threaded portion passage
13. Branch
14. Cylindrical body
15. Slot
16. Cylindrical body distal part
17. Ridge
18. Groove
19. Screw extender internal threaded part
20. Multi-use instrument lower part
21. Conical part
22. Blade
23. Half tube
24. Screw driver
25. Handle
26. Multi-use instrument (Rod reduction/Set screw driver/screw release)
27. Rod inserting instrument
28. Breakable pin
29. Lateral pin
30. Circular groove
31. Puncturing needle/Guide wire
32. Concave screw top
33. Convex upper half ball The examples below more precisely relate to a thoracolumbar fusion system consisting of pedicle screws and rods combined with single use instruments. A typical pedicle screw system consists of the screw implants and the instruments for placing the screws.

FIG. 1 shows an example of an implant kit according to the invention.

This kit contains a tissue dilatation sleeve 9, a handle 25, a rod 7, a rod inserting instrument 27, a shaft 26 which can be used as a rod reduction instrument and/or a set screw driver and/or a screw releasing instrument, a pedicle screw 1, a screw extender 6 and a screw driver 24.

Figure 2:
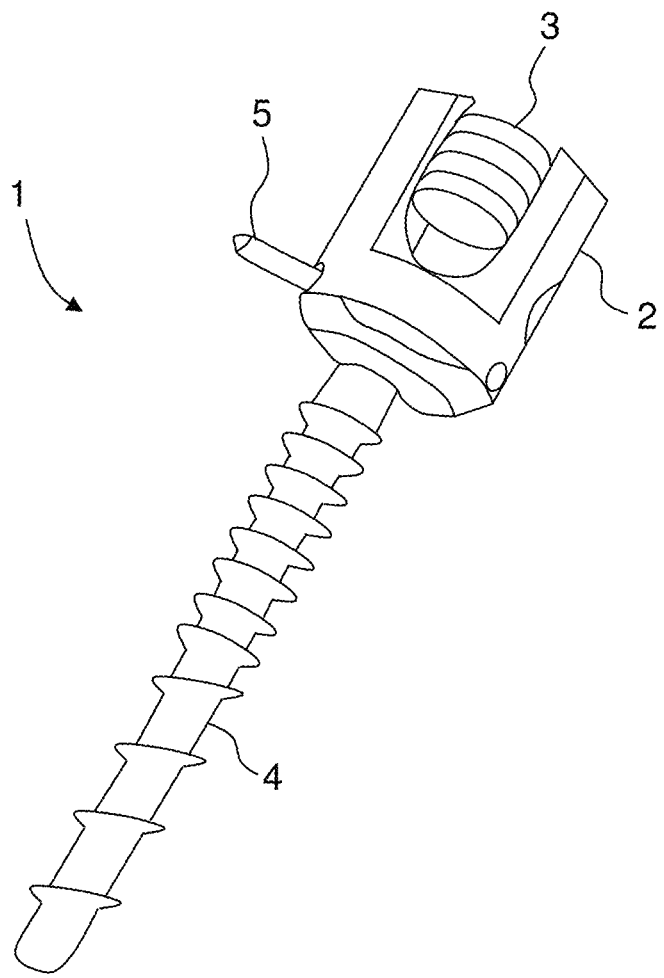
FIG. 2 shows an example of a lockable poly-axial pedicle screw according to the invention
Figure 3C:
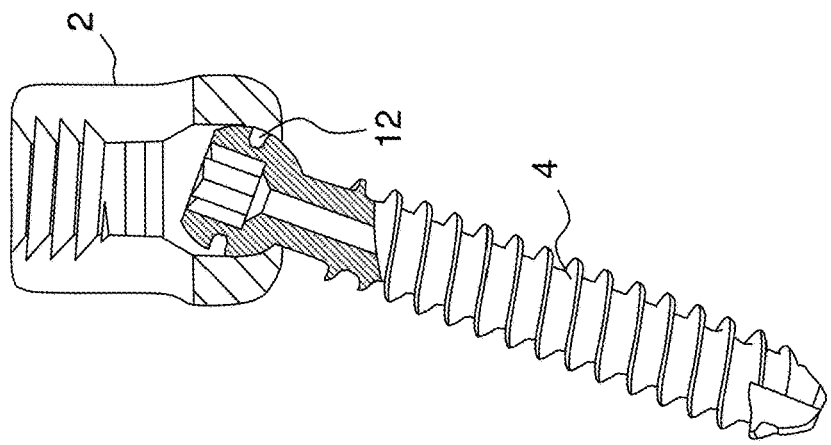
FIGS. 3A to 3C are cross-sections and partial cut views of the screw of FIG. 2
Figure 3B:
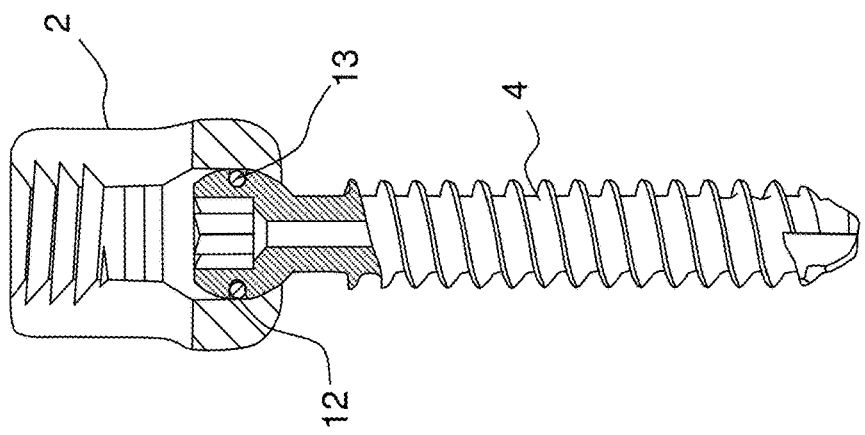
Figure 3A:
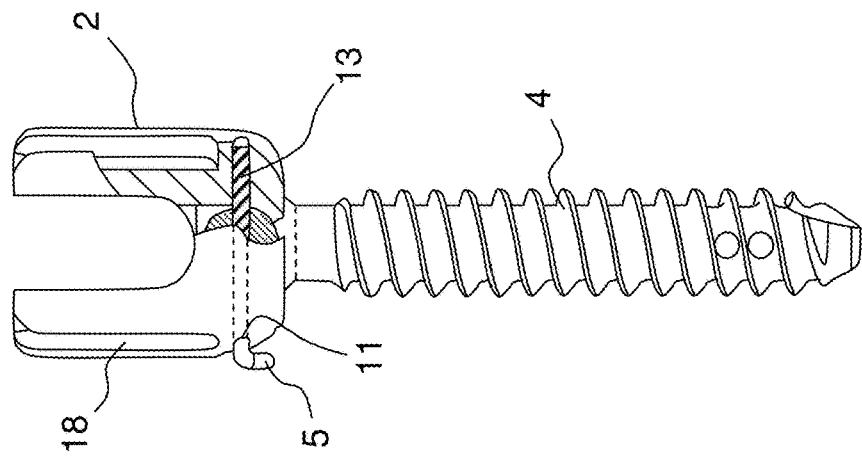
Figure 4:
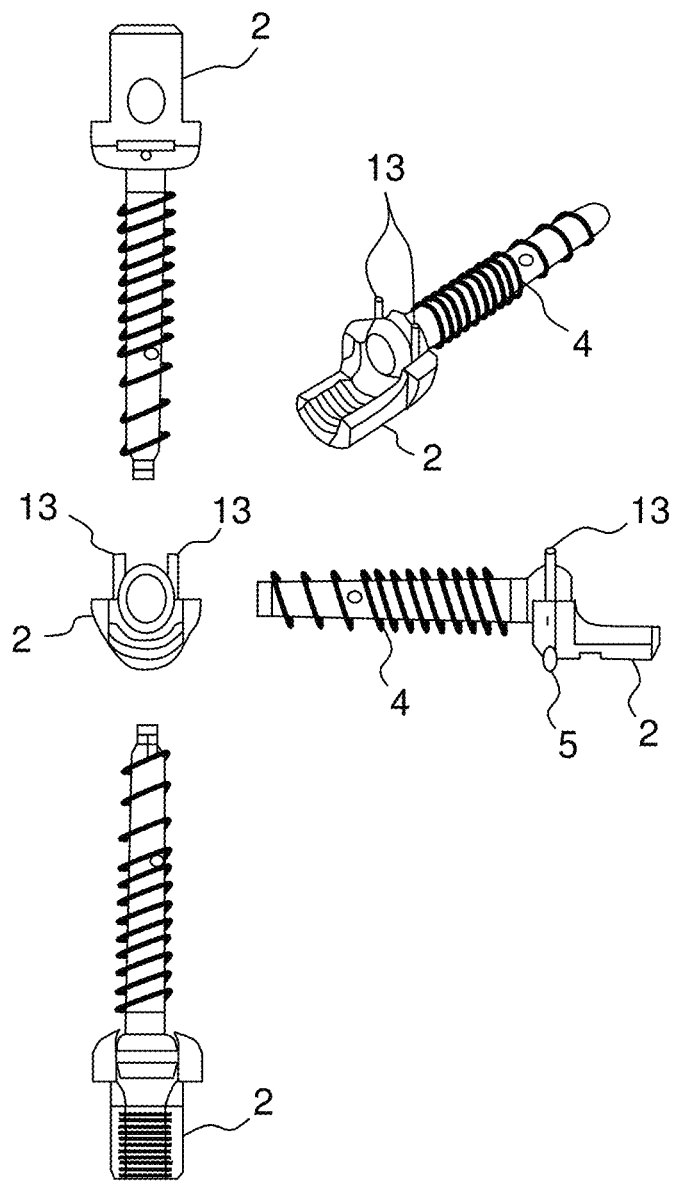
FIG. 4 represents different views (complete and partial) of the screw of FIG. 2

The lockable poly-axial screw 1 illustrated in particular in FIGS. 2 to 4 includes a head 2 and a threaded portion 4. FIG. 2 also shows a set screw 3 which may be fixed to the head after the insertion of a rod 7. The screw 1 furthermore comprises a locking element 5 having a U-shape. When the locking element 5 is fully inserted in the screw head 2 the orientation of threaded portion 4 is blocked with respect to the head 2. Inversely, when the locking element is retrieved, the threaded portion 4 can be freely oriented with respect to the screw head 2.

The lockable poly-axial screw according to the invention may therefore be transformed into a mono-axial screw, thus allowing having mono-axial and poly-axial capability in the same product. A blocking system defined previously allows the surgeon to choose if he/she wants to use the screw in mono-axial or poly-axial mode. As mentioned mono-axial capability is achieved by pushing the locking element (clip) 5 and poly-axial capability is achieved by removing the clip 5. The clip 5 is just an example of a blocking system; other technical solutions can also be imagined such as a pin.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

Any orientation of the axis can be considered when the mono-axial is used, i.e. the screw axis and the screw head may be oriented along different directions.

Figure 5:
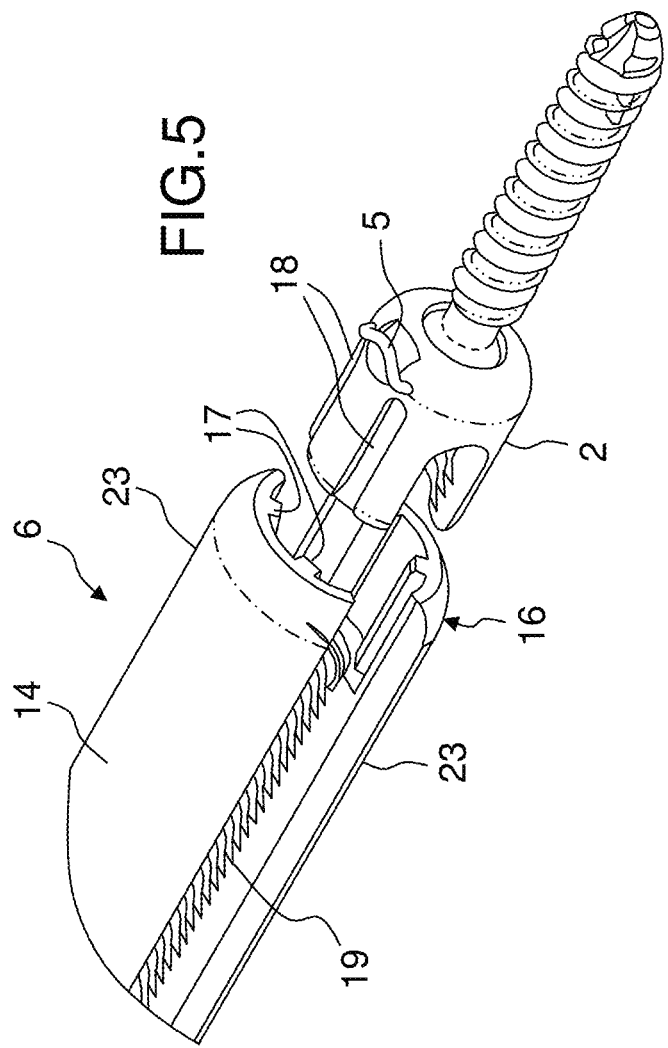
FIG. 5 shows the distal part of a screw extender according to the invention, together with the screw of FIG. 2
Figure 6:
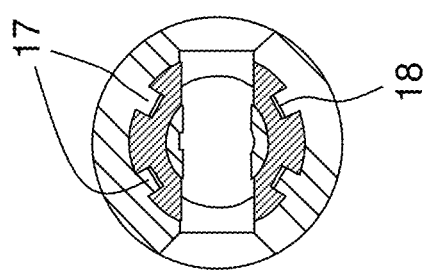
FIG. 6 is a cross section of the screw extender distal part
Figure 7:
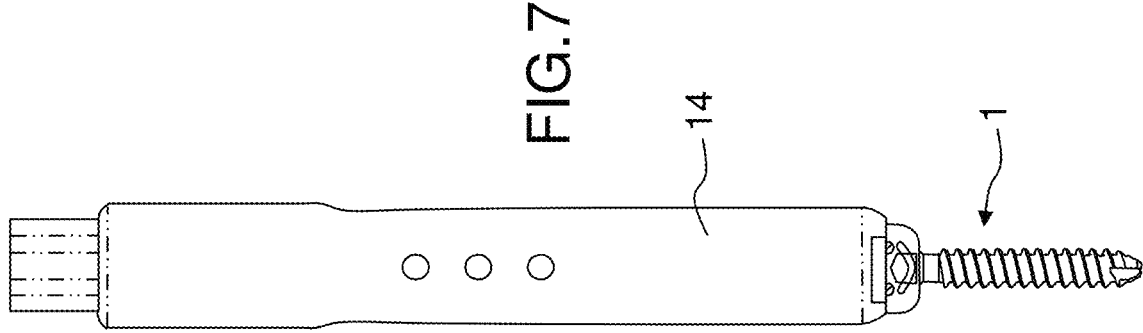
FIG. 7 is a global view of a screw extender with a screw

FIGS. 5 to 7 represent the attachment of a pedicle screw 1 to the distal end 16 of a screw extender 6, by inserting the screw head 2 within the distal end 16. In this operation the head 2 is guided with a lurality of ridges 17 located within the distal end 16 and grooves located on the head 2. With such a system the screw head is better retained within the screw extender 6.

Any suitable material can be used for the screw extender 6 (plastic, polymer, metal, etc . . . ).

Figures 8A, 8B, 8C:
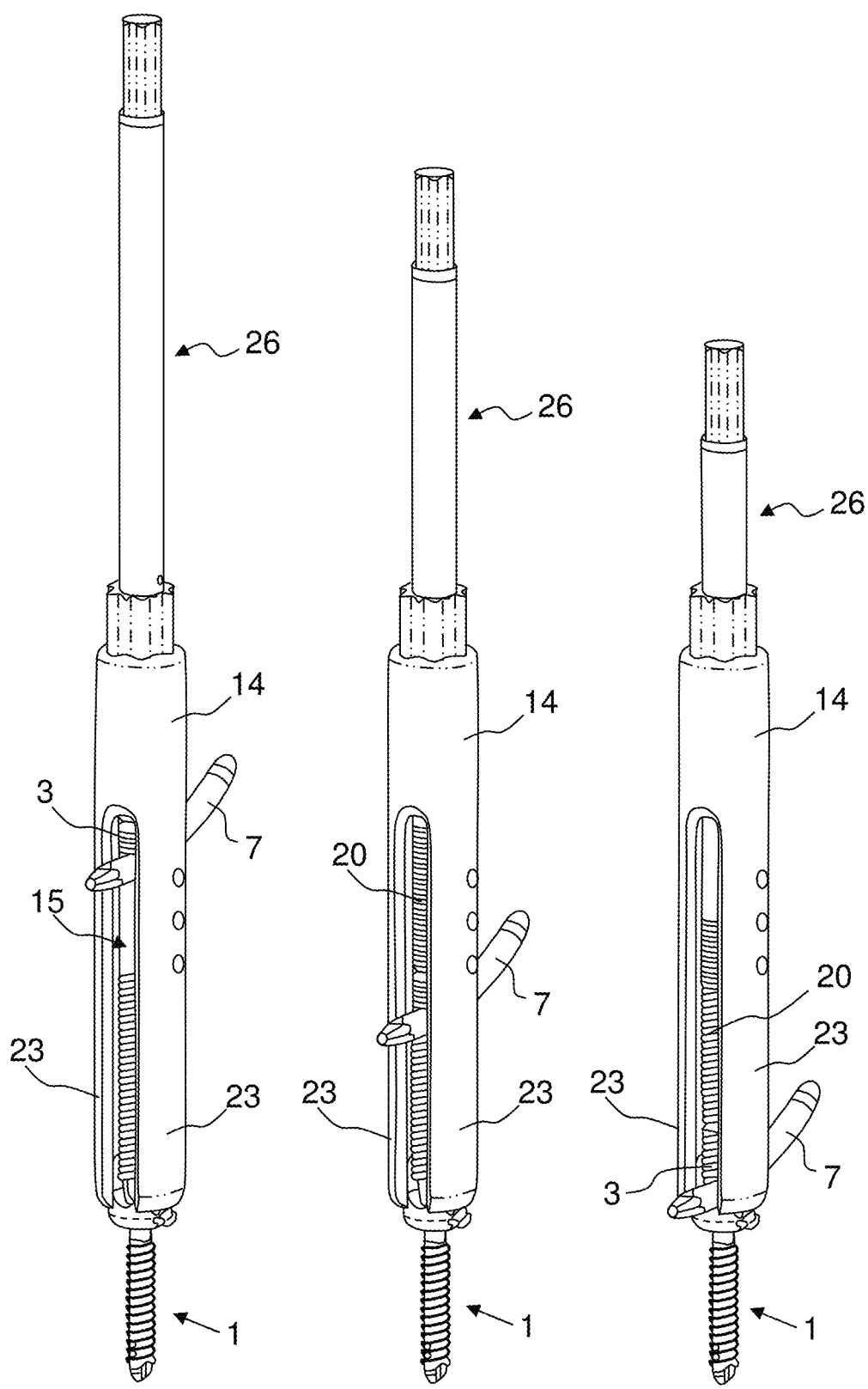
FIGS. 8A to 8C represent the positioning of the rod in the screw head, rod reduction and the tightening of the set screw

FIGS. 8A to 8C represent the positioning of the rod 7 in the screw head 2, a rod reduction and the tightening of the set screw 3 in the screw head 2.

Figure 13A:
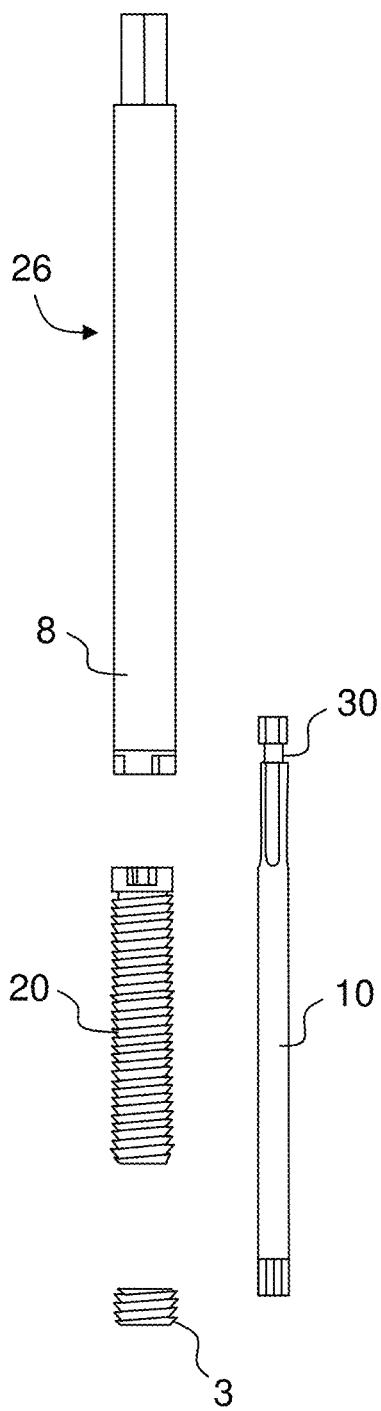
FIGS. 13A to 13C show different views of a rotatable shaft which is used in a rod reduction instrument, a set screw driver and a screw releasing instrument
Figure 13B:
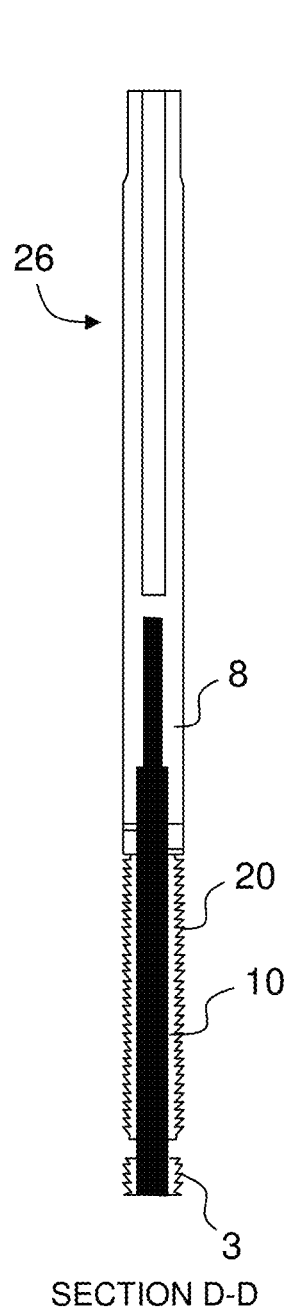
Figure 13C:
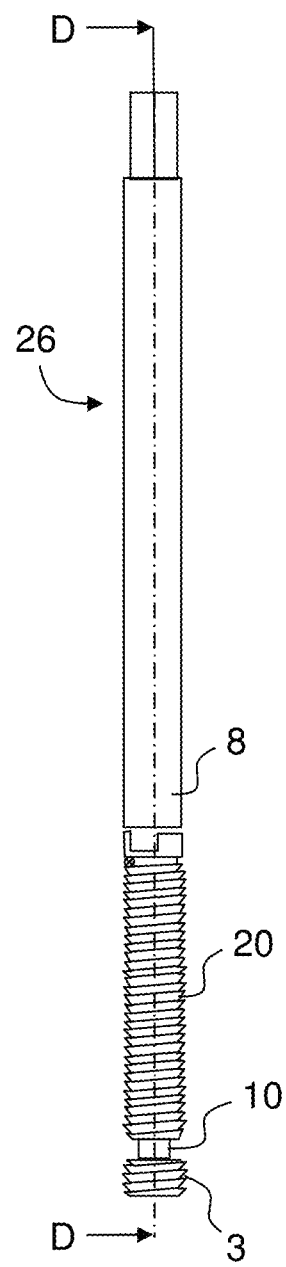

The multi-use instrument 26 (see also FIGS. 13A to 13B) is defined by an upper part 8 and a lower (threaded) part 20.

The rod 7 may be pushed downwards by rotating the multi-use instrument 26 within the cylindrical body 14.

After the rod insertion within the head 2, the set screw 3 is fixed to the head 2 by further rotating the multi-use instrument 26.

Figure 9A:
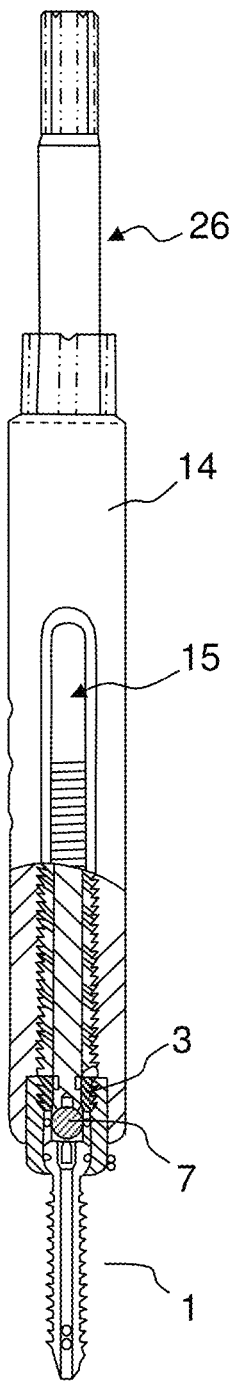
FIGS. 9A to 9C illustrate the release of the screw with respect to the screw extender
Figure 9B:
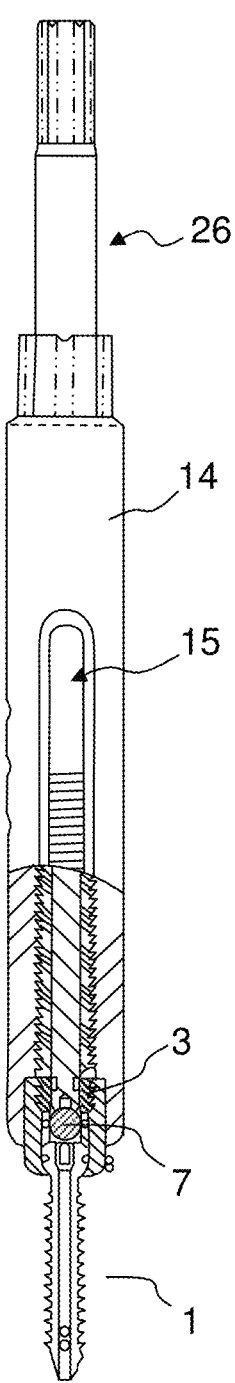
Figure 9C:
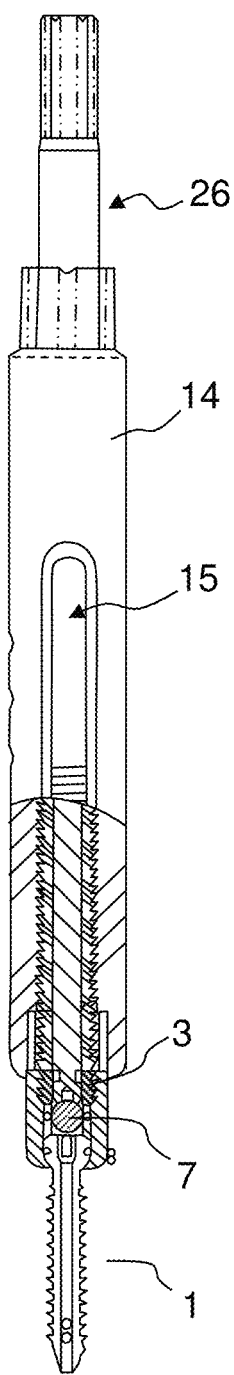
Figure 14:
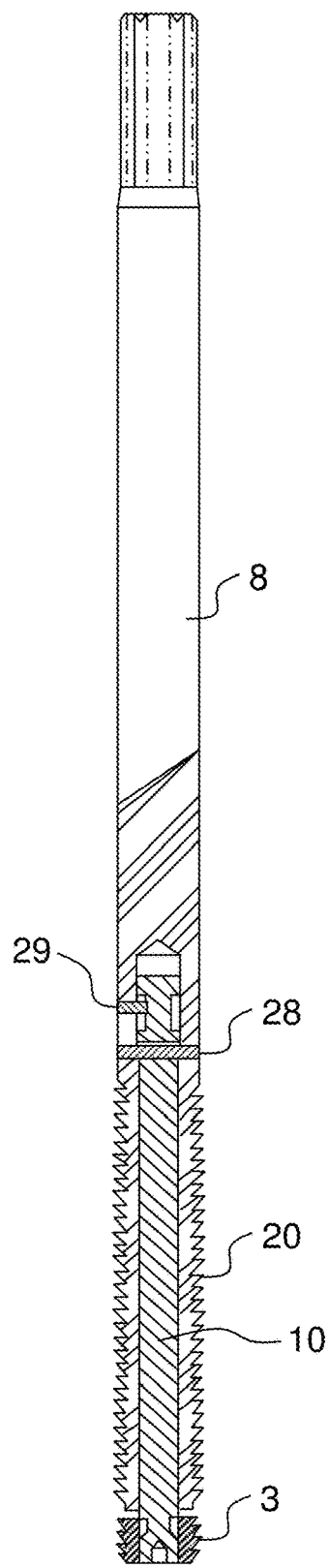
FIGS. 14 and 15 illustrate a torque limiting mechanism
Figure 15:
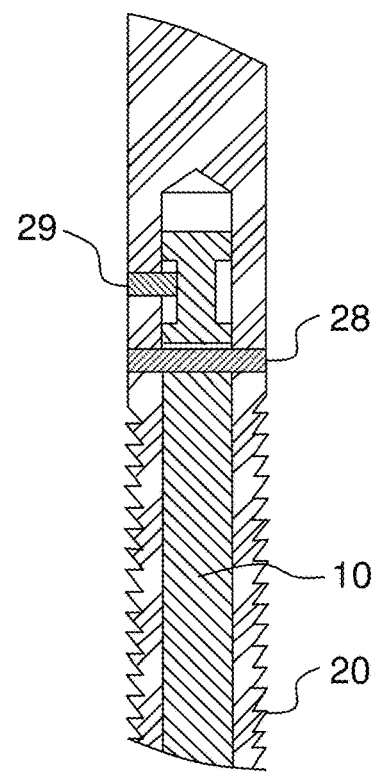

The multi-use instrument 26 is also provided with a torque limiting mechanism (see FIGS. 14 and 15). When the set screw 3 is fixed within the head 2 and the multi-use instrument 26 further rotated, the torque increases, up to a point where the pin 28 breaks. A further rotation of the multi-use instrument 26 has therefore no more effect on the set screw 3. From that point the further rotation of the multi-use instrument 26 only induces a downwards pressure on the screw head 2. The screw 1 is therefore progressively separated from the screw extender (see FIGS. 9A to 9C).

This screw releasing mechanism from an instrument offers the possibility to release the screw 1 from the screw extender without laterally expanding the screw extender 6.

It should be mentioned at this stage that this mechanism is not limited to the release of pedicle screws. Any other item may be used.

To summarize, the same instrument 26 can be used for rod reduction, for fixing a set screw to a screw head and for releasing a screw from a screw extender.

It should be underlined that the invention is not limited to this triple use of the same instrument. A double use is also comprised, for instance rod-reduction and fixation of the screw set to the screw head.

Figure 10:
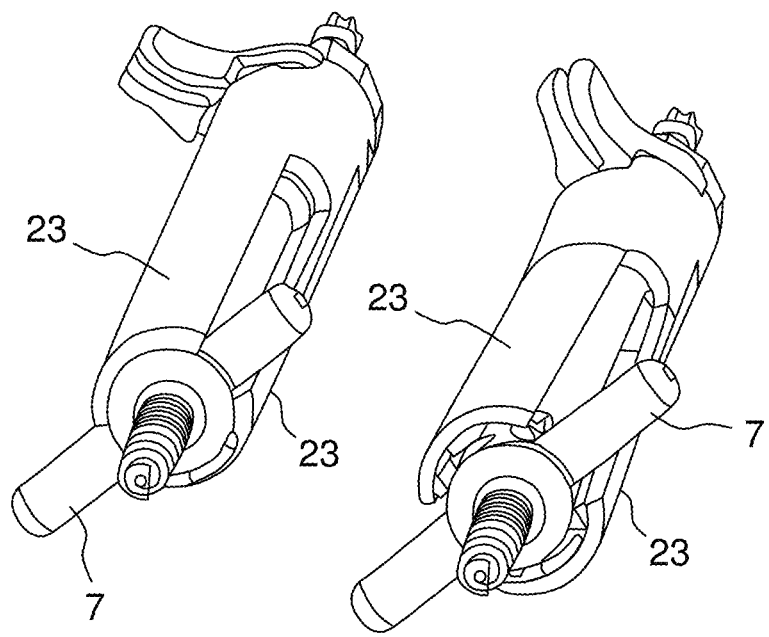
FIG. 10 shows a screw extender which includes a mechanism for laterally expanding the screw extender distal part
Figure 11:
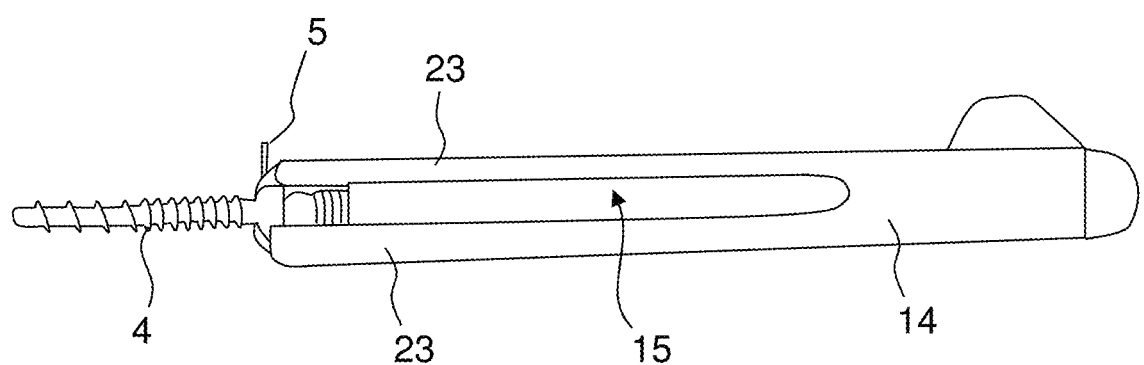
FIG. 11 is another representation of the screw extender of FIG. 10

FIGS. 10 and 11 show an alternative solution to attach a pedicle screw to an screw extender, by rotating an inside tube (not illustrated) the half-tubes 23 are expanded by their own elasticity. This allows a screw to be inserted and fixed to it by for example clamping the outer surface around the screw. The same principle can be used as an alternative to detach the screw extender from a screw.

The clamping system also achieves part of its rigidity, by resting on support surfaces on the screw head.

Figure 12:
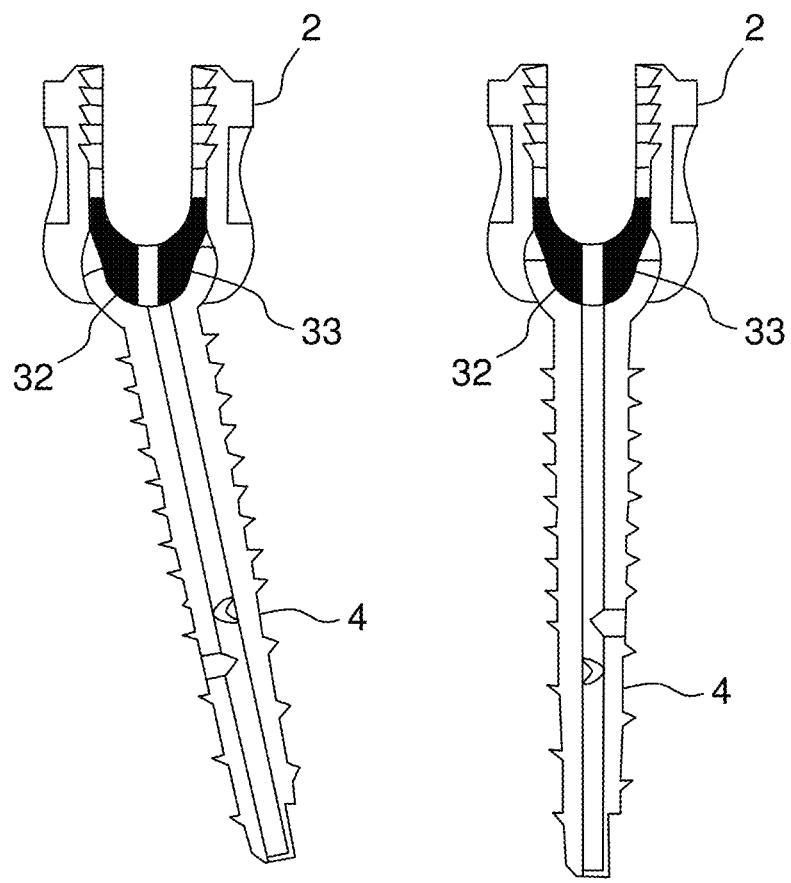
FIG. 12 shows another embodiment of a pedicle screw according to the invention

FIG. 12 shows a concave screw top 32, inside a convex upper half ball 33, allowing the rod 7 and the set screw 3 to be set lower in the screw head 2, thus decreasing the total build height, and increasing the strength and rigidity of the system.

Figure 16:
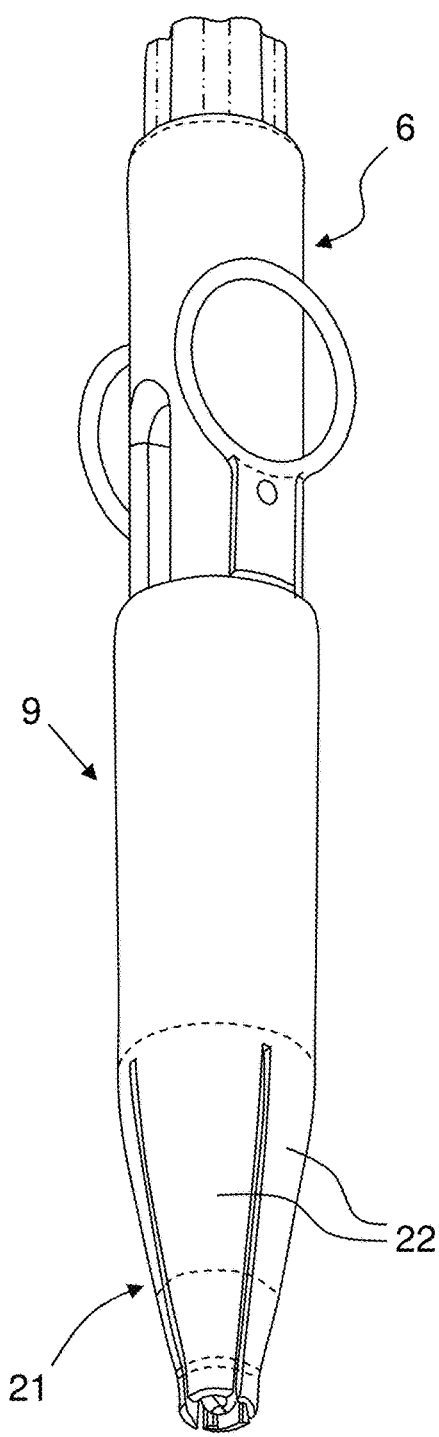
FIGS. 16 and 17 show the use of a tissue dilatation sleeve
Figure 17:
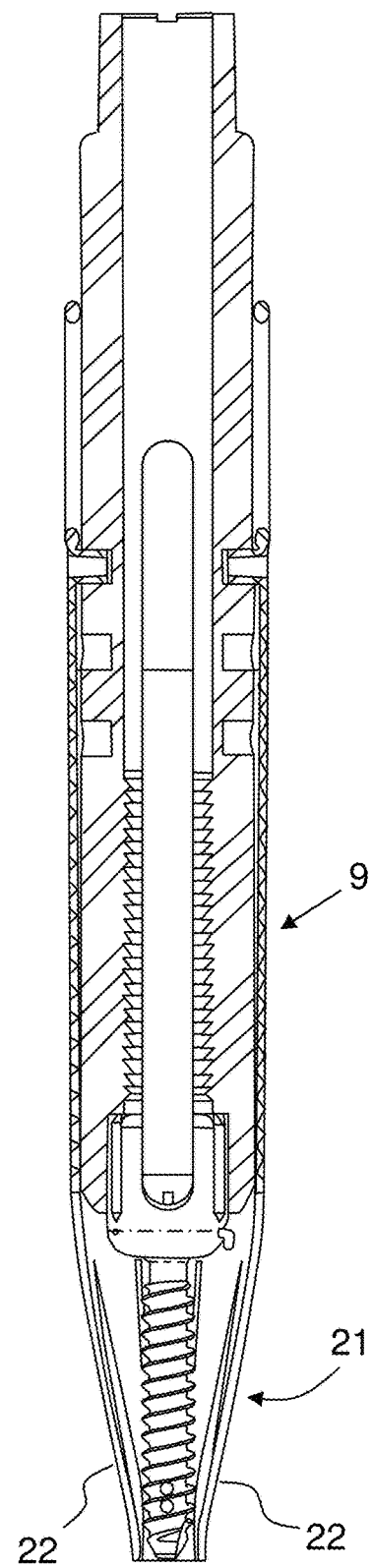
Figure 19:
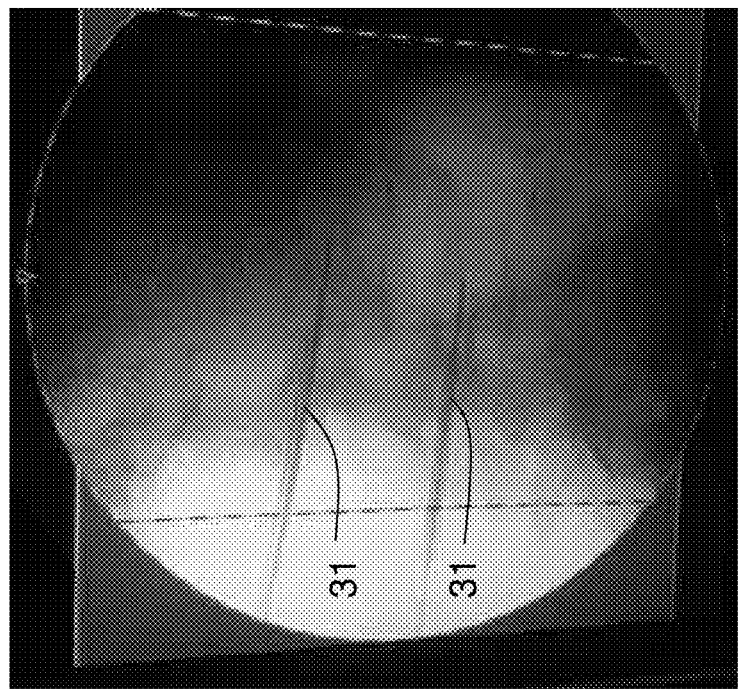
FIGS. 18 to 38 show a procedure using an implant kit according to the invention
Figure 18:
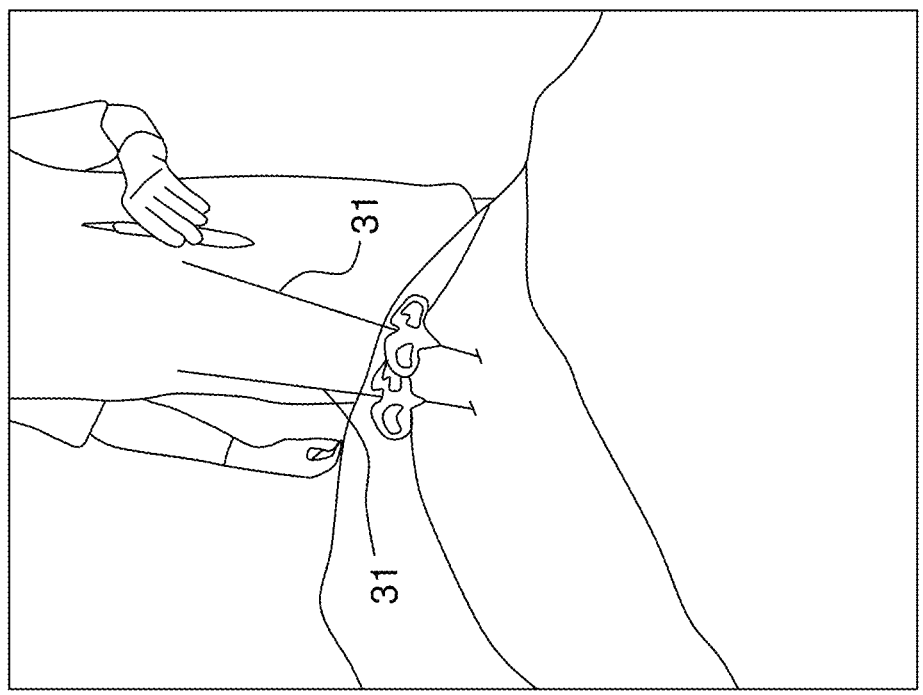
Figure 21:
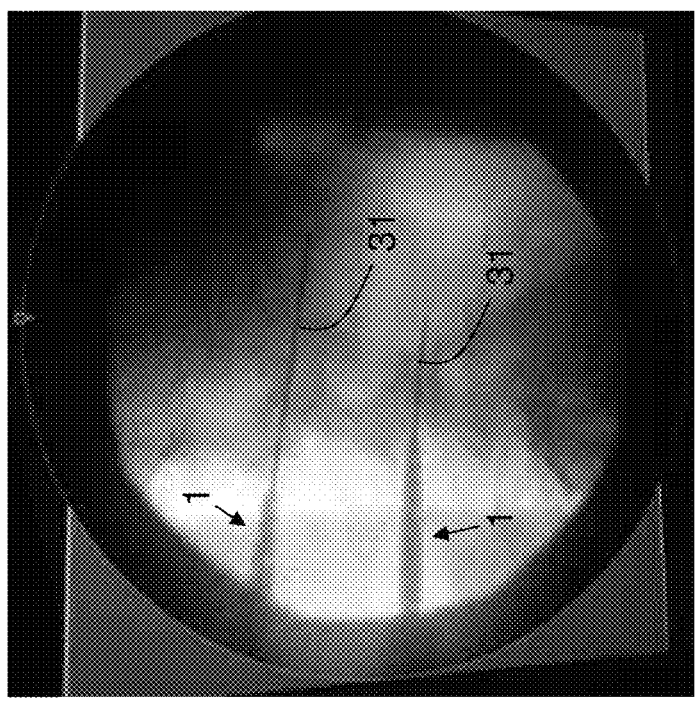
Figure 20:
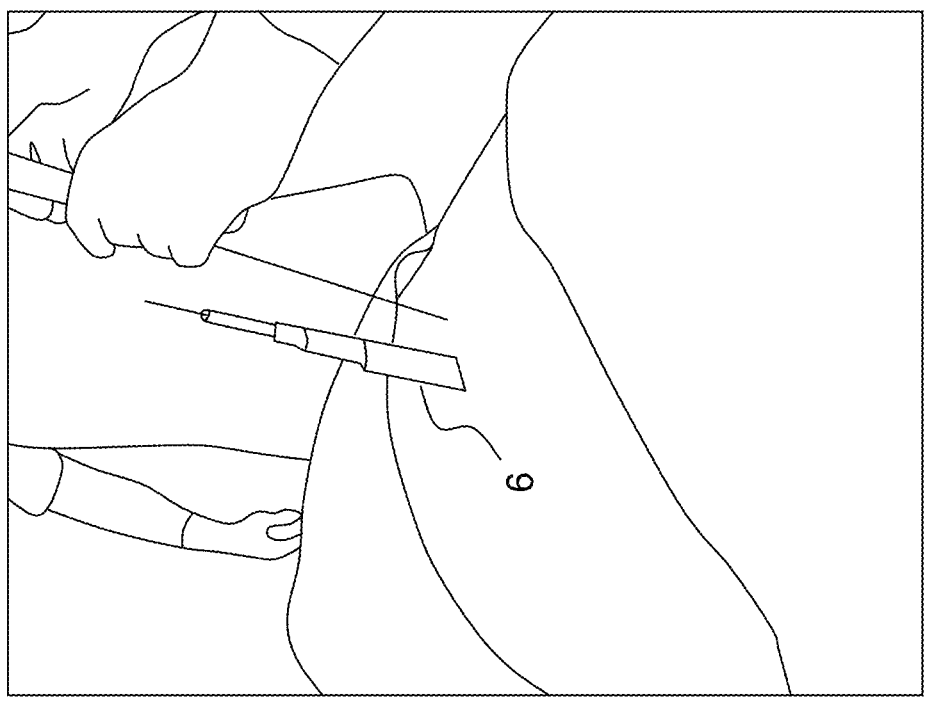

FIGS. 16 and 17 represents a tissue dilatation sleeve 9 containing four triangular flexible blades 22 intervened into each other and forming a cone 21. The cone 21 is mounted at the tip of a screw extender 6, with a tear off spiral. This allows the tissue to be pushed aside as the screw extender 6 is inserted into a body. Once in place, the surgeon may remove the sleeve 9 while the screw extender remains in the body. Any suitable number of blades can be used for forming the cone.

FIGS. 18 to 38 show a procedure using the items which have been previously presented.

In a first step (FIGS. 18 and 19) two puncturing guide wires 31 are positioned in the spine.

A first screw extender 6 with a screw 1 attached and surrounded by a dilatation sleeve is then inserted through the tissue (FIGS. 20 and 21), and along the guide wire 31. The screw extender 6 is rotated and/or pushed.

Figure 23:
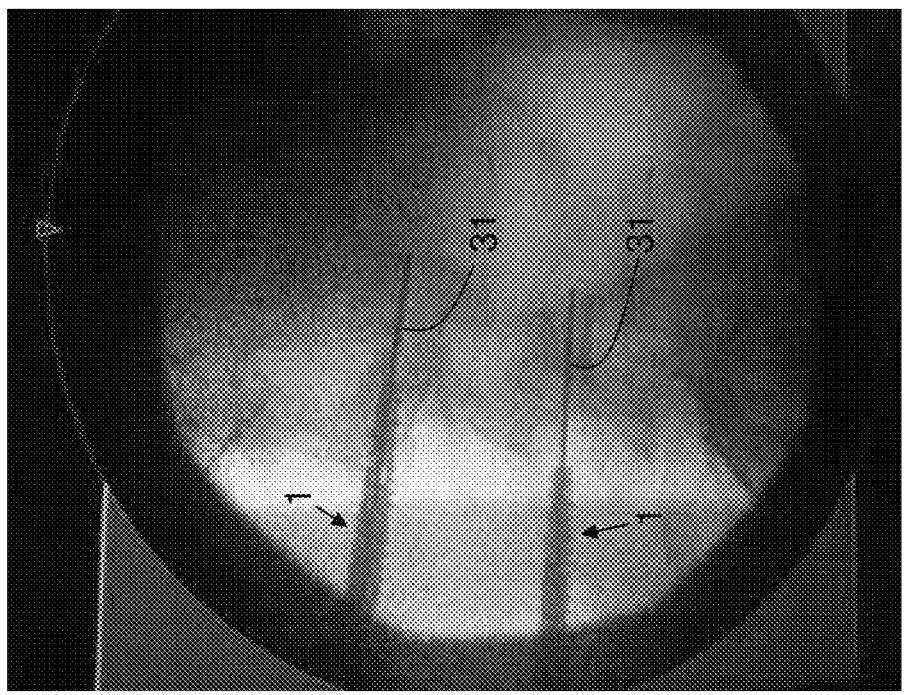
Figure 22:
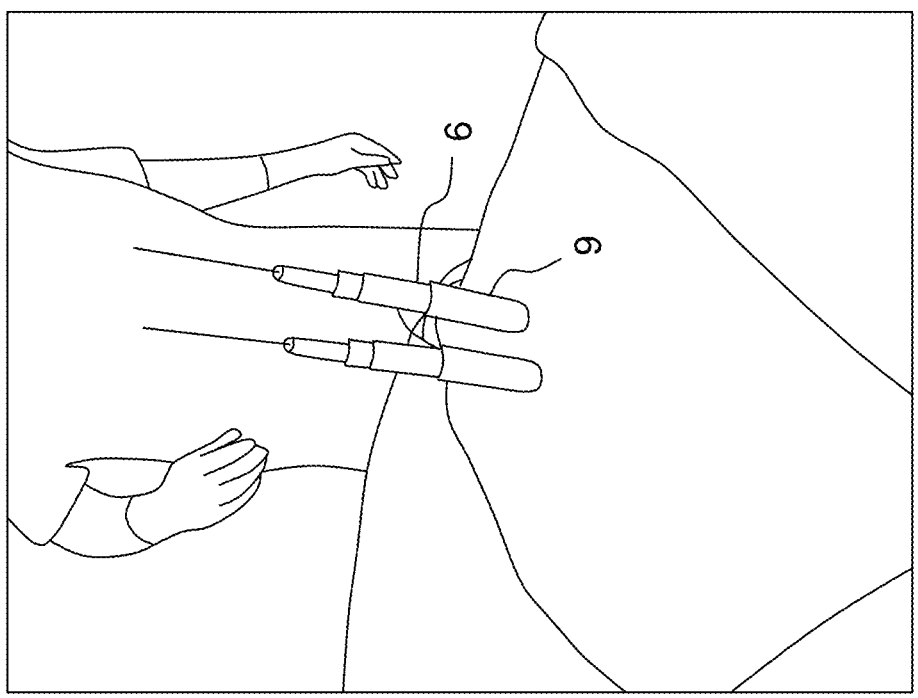

A similar operation is carried out with a second screw extender 6 and screw 1 (FIGS. 22 and 23).

Figure 25:
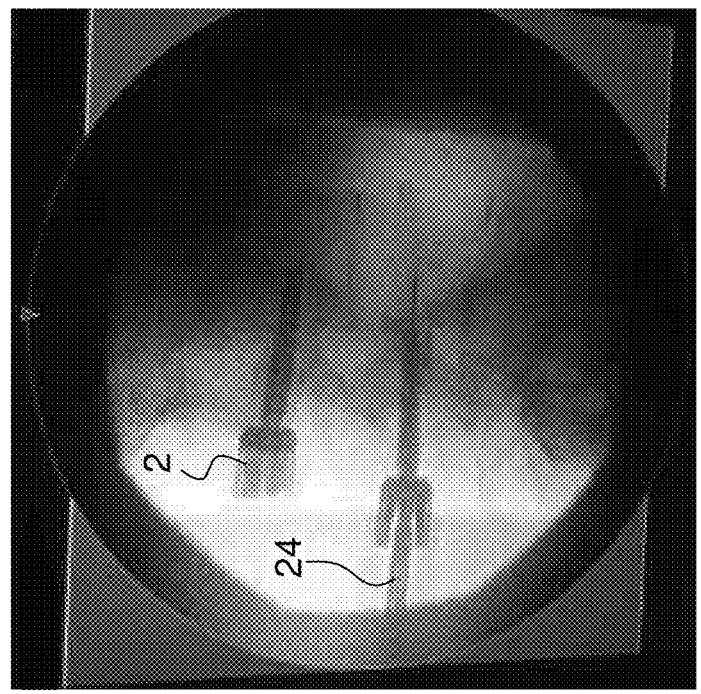
Figure 24:
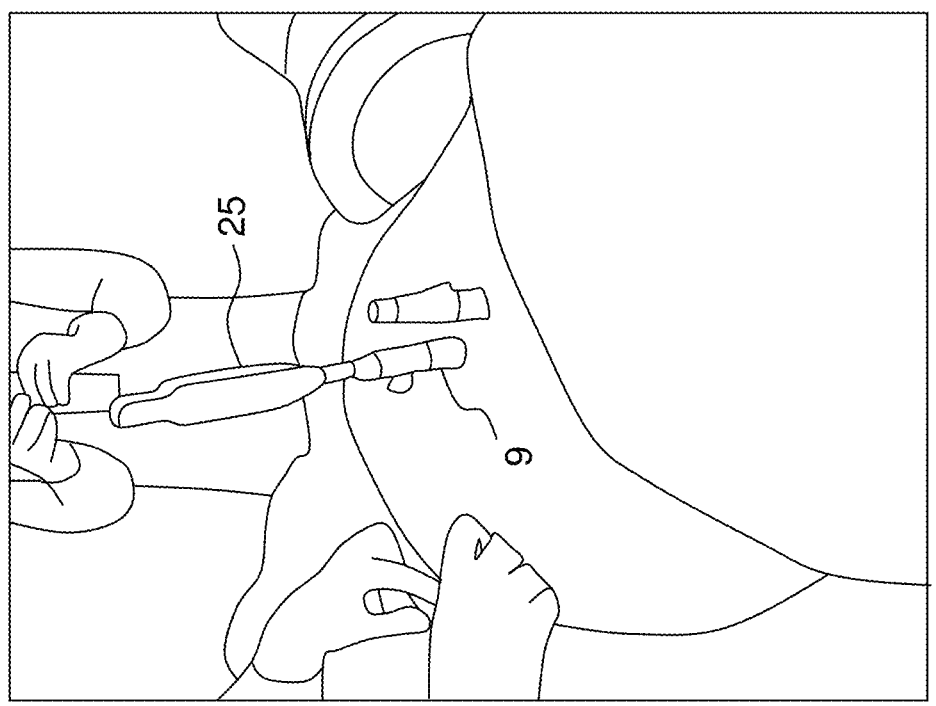

A screw driver 24 is inserted within the screw extender 6. Its distal end is introduced within the upper part of the screw threaded portion 4. The screws 1 are then rotated and enter the vertebrae (FIGS. 24 and 25).

Figure 27:
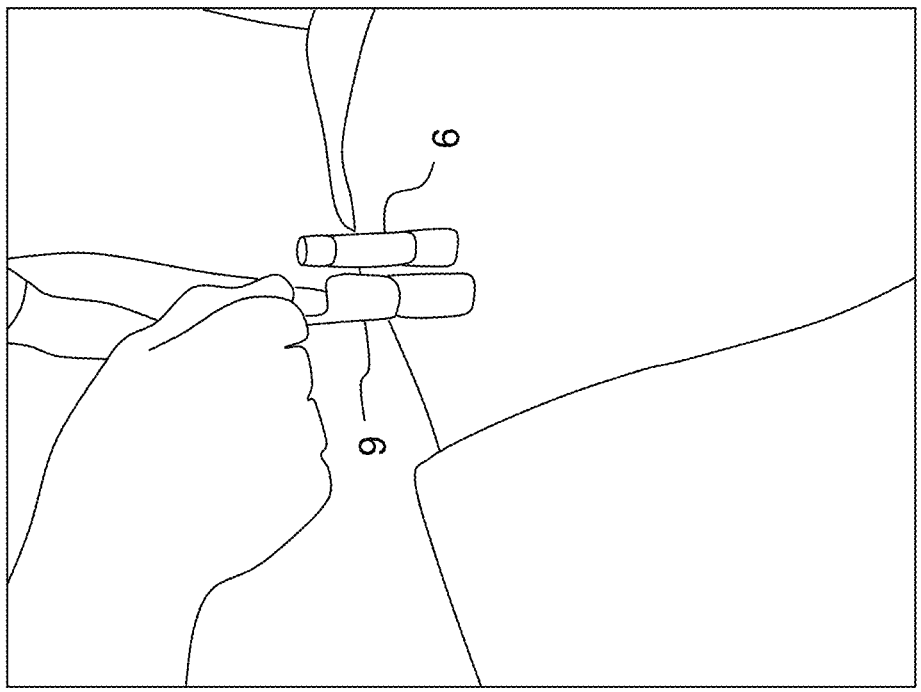
Figure 26:
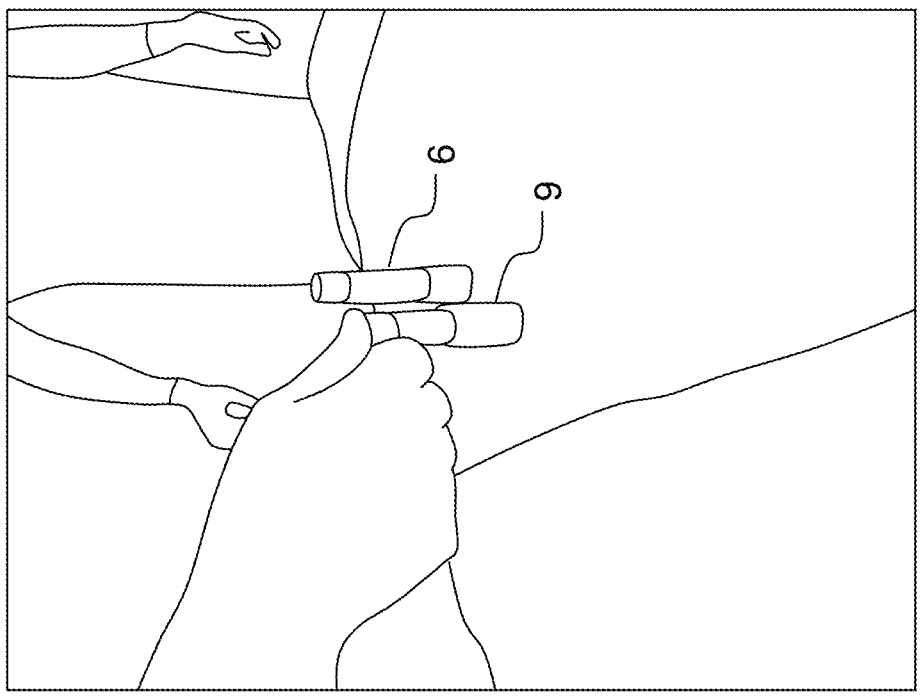
Figure 28:
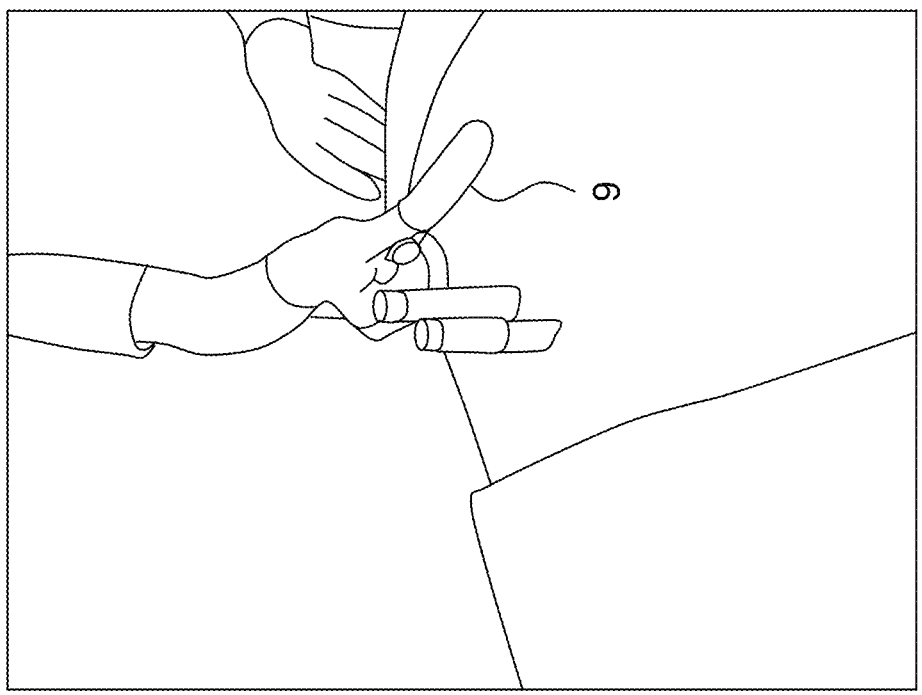

The tissue dilatation sleeves 9 are removed (FIGS. 26 to 28).

Figure 30:
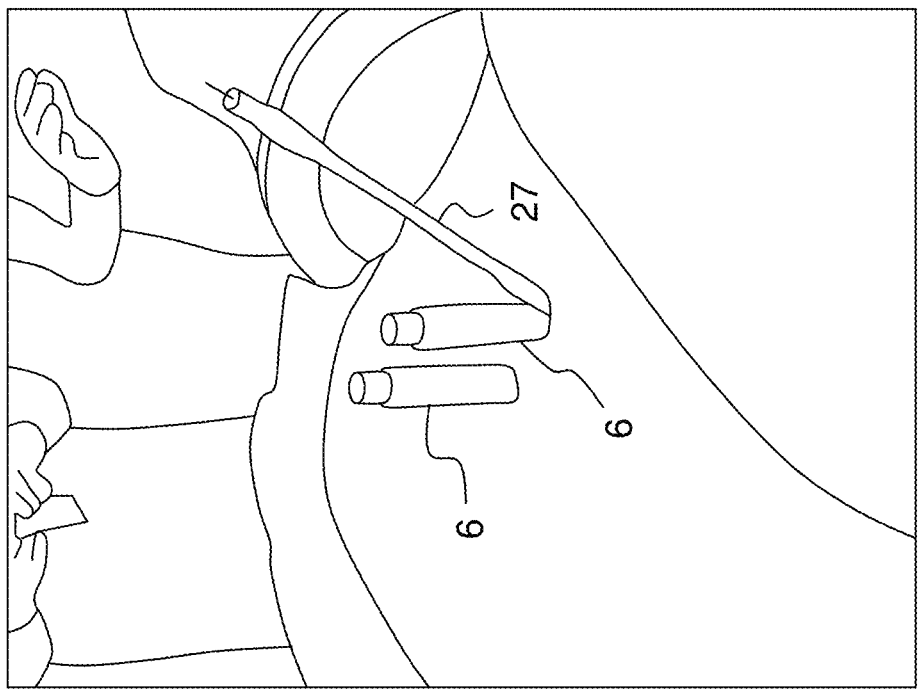
Figure 29:
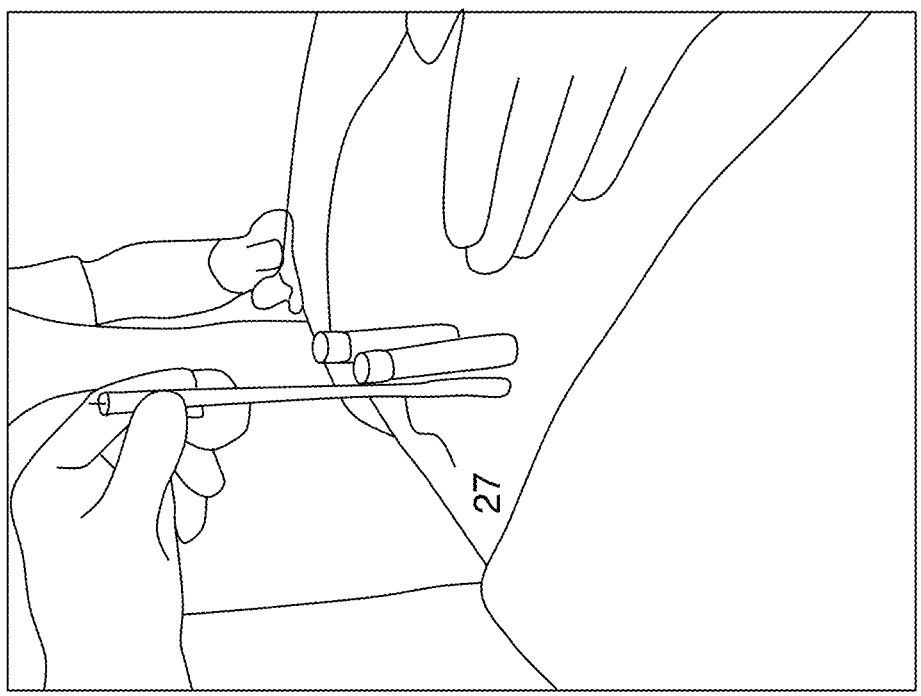

A rod inserting instrument 27 with a rod 7 at its end is transversally crossing the tissue (FIGS. 29 and 30).

Figure 32:
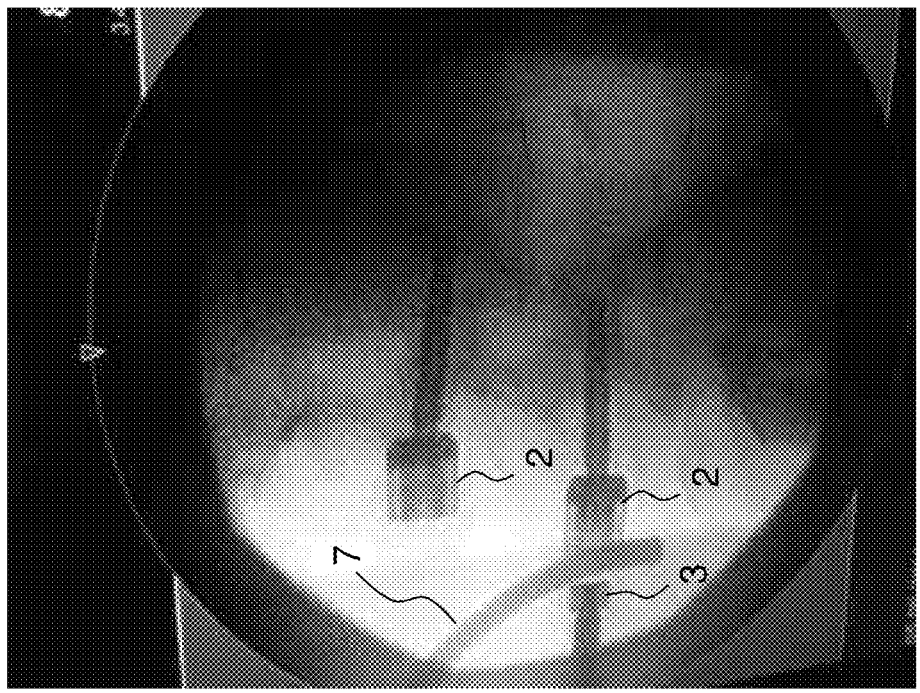
Figure 31:
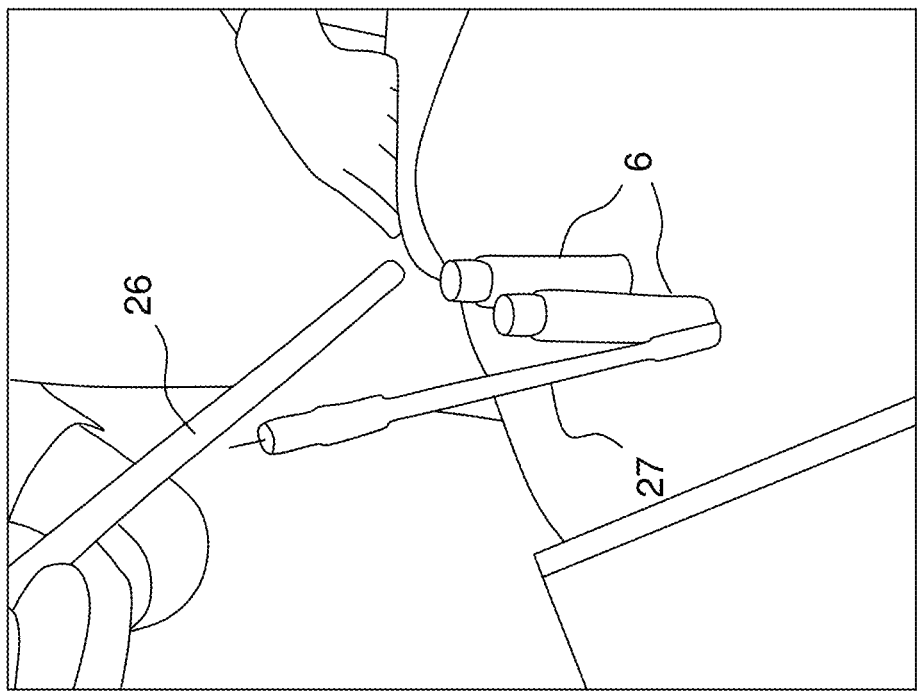
Figure 34:
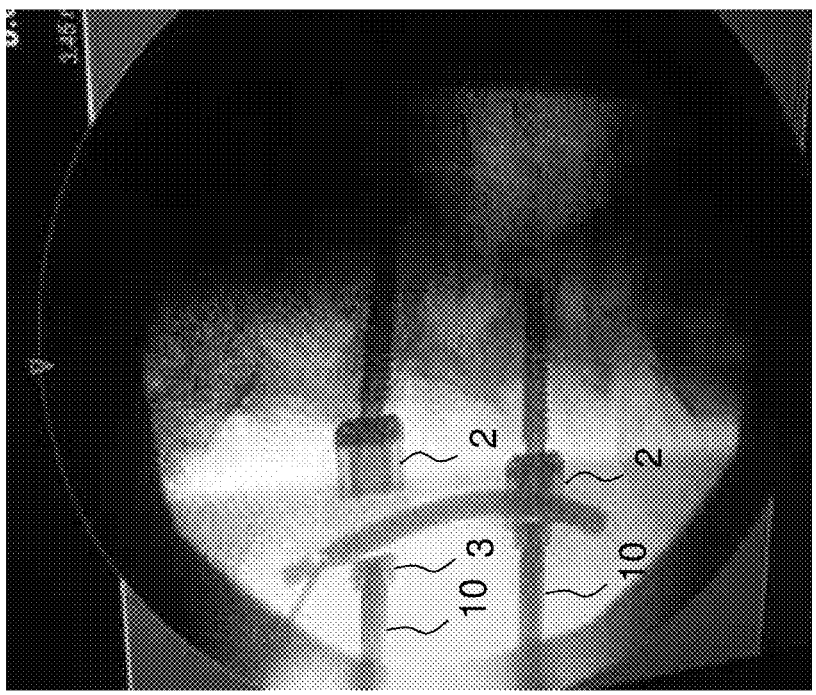
Figure 33:
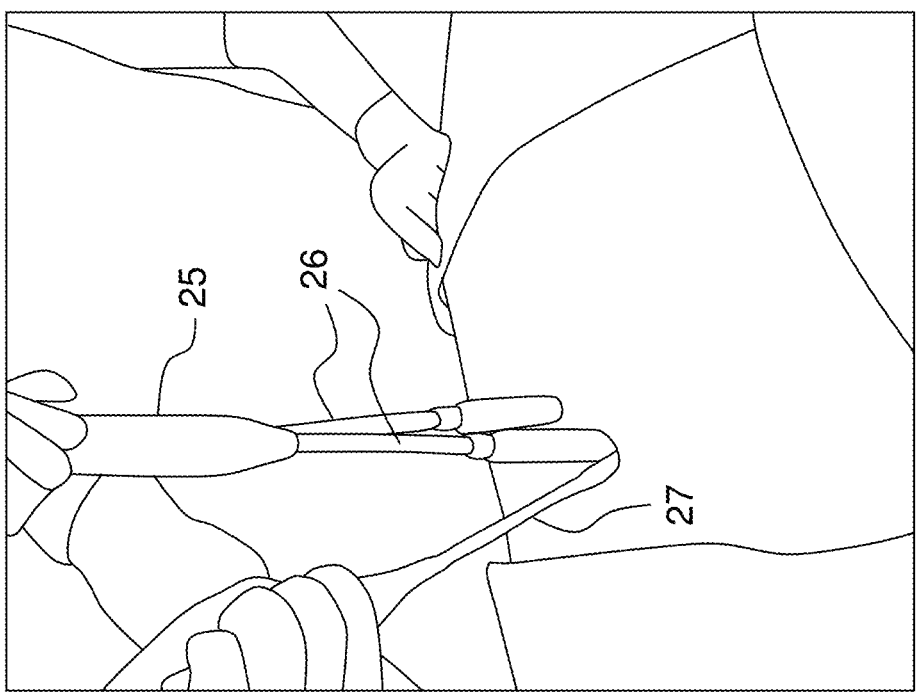
Figure 36:
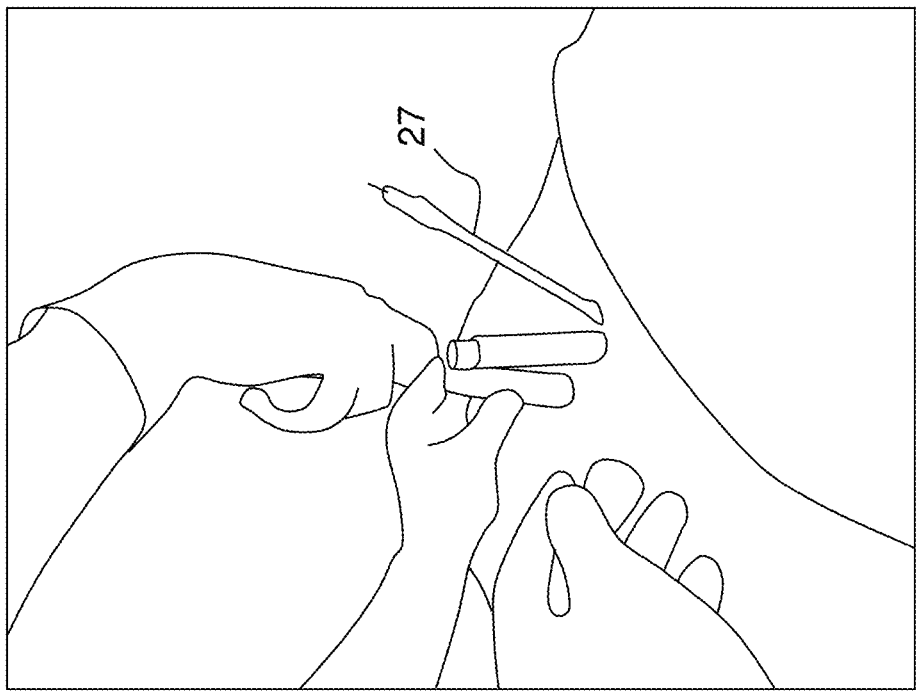
Figure 35:
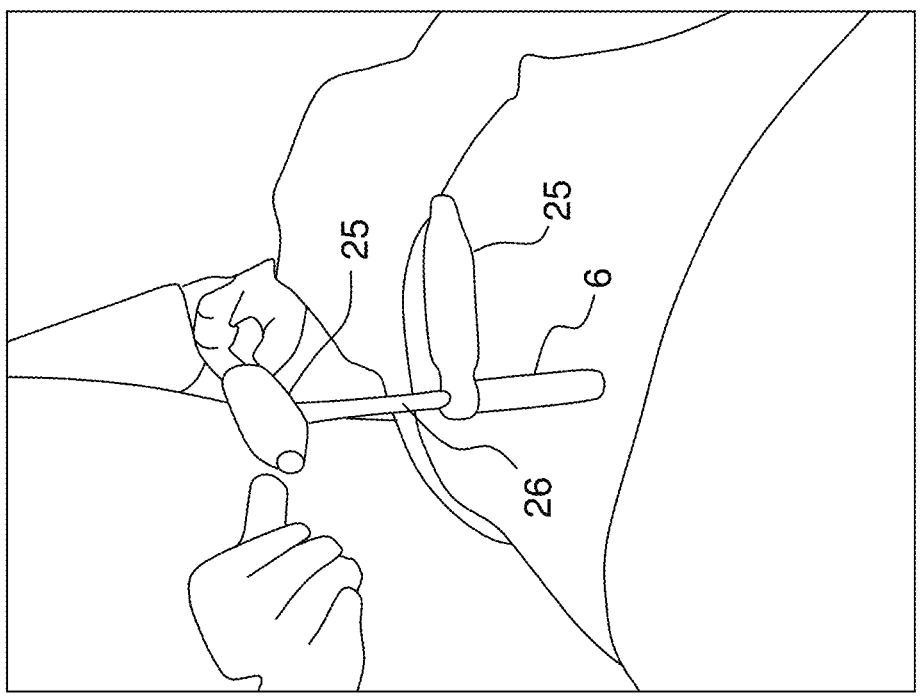

The rod 7 is positioned above the screw head 2 (FIG. 32) and the multi-use instrument 26 is introduced within the screw extender 6, to such an extent that the set screw 3 is positioned above the rod 7, in line with the screw head 2 (FIGS. 31 and 32).

FIGS. 33 to 36 show the rod placement within the screw heads 2 and the fixation of the set screw 3 within the screw head 2.

Figure 38:
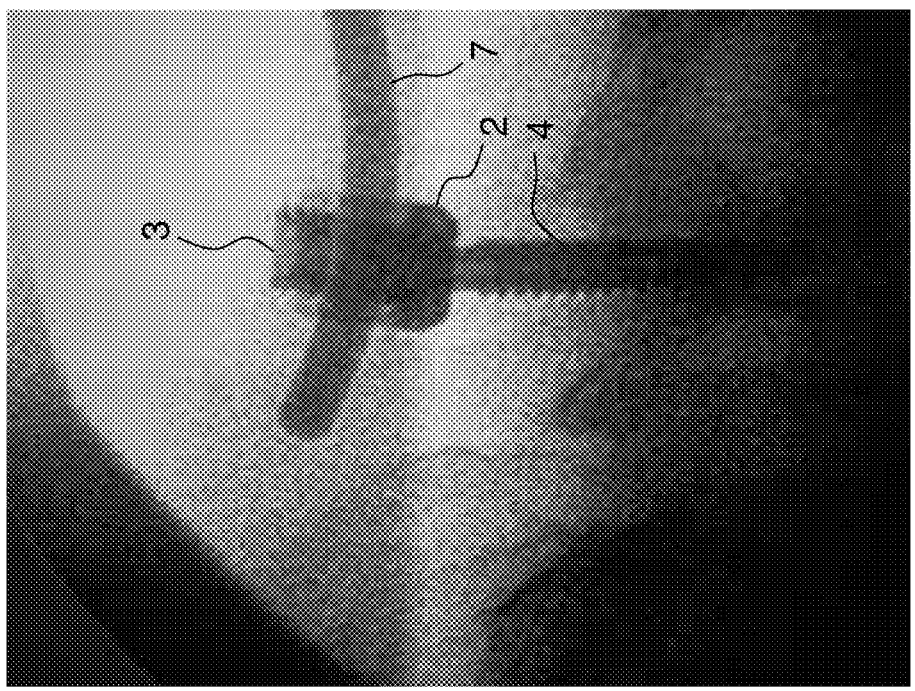
Figure 37:
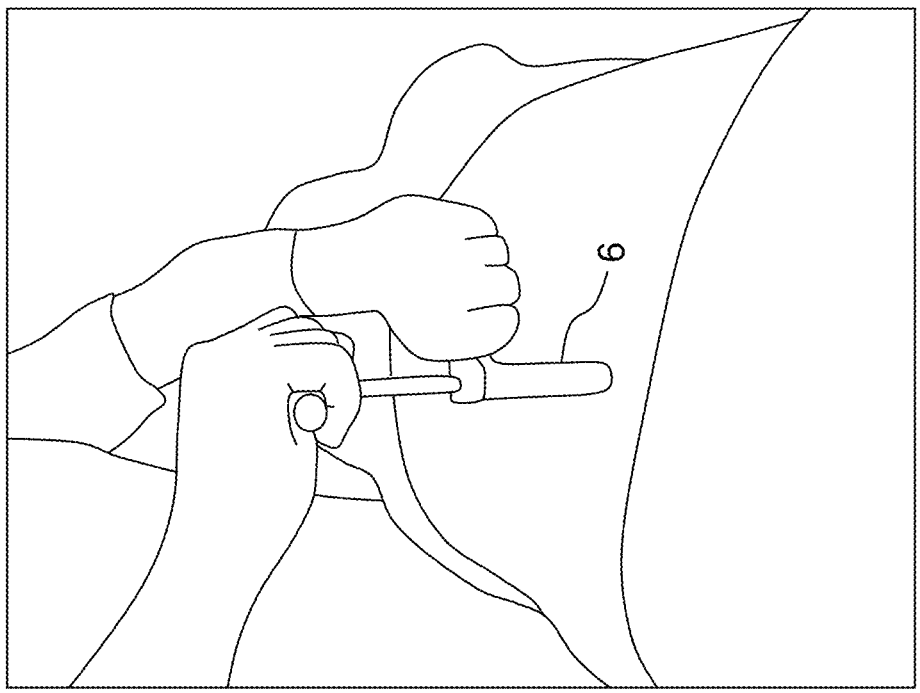

FIGS. 37 and 38 illustrate the screw release from the screw extender 6 and the screw 1, the rod 7 and the screw set 3 in their definitive location.

The invention is of course not limited to those illustrated examples.

The screw extender according to the invention may be used with mono-axial, poly-axial or lockable poly-axial screws.

The invention claimed is:

1. An orthopedic screw extender comprising:
a hollow longitudinal body including two opposite longitudinal slots, a distal part of the hollow longitudinal body having an engagement mechanism configured to receive a screw head by an upwardly pressure on the screw head in a direction of a main axis of the hollow longitudinal body towards the hollow longitudinal body, and configured to separate from the screw head by a downward pressure on the screw head away from the hollow longitudinal body; and
a screw release instrument having an external thread,
wherein the hollow longitudinal body includes an internal thread, the internal thread configured to threadably engage with the external thread of the screw release instrument to provide the downward pressure to the screw head.

2. The screw extender according to claim 1, the engagement mechanism includes a longitudinal ridge or a longitudinal groove arranged in parallel to the main axis at the distal part of the hollow longitudinal body, dimensioned to receive a corresponding longitudinal groove or longitudinal ridge, respectively, of the screw head.

3. The screw extender according to claim 1, wherein the hollow longitudinal body is configured to threadably engage by the internal thread with an external thread of a multi-use instrument or a threading of a set screw inside the hollow longitudinal body.

4. The screw extender according to claim 1, wherein the engagement mechanism is configured to guide the screw head during an insertion to the screw extender along the direction of the main axis of the screw extender.

5. The screw extender according to claim 1, wherein the hollow longitudinal body is made of one piece of elastic material.

6. The screw extender according to claim 1, wherein the engagement mechanism is configured such that the downward pressure on the screw head by the screw release instrument progressively separates the screw head from the screw extender.

7. The screw extender according to claim 1, wherein the engagement mechanism is configured such that the downward pressure on the screw head by the screw release instrument progressively separates the screw head from the screw extender without laterally expanding the screw extender.

8. An implant kit having the orthopedic screw extender according to claim 1.

9. The screw extender according to claim 1, wherein the two opposite longitudinal slots include an open end towards the distal part of the hollow longitudinal body.

10. An orthopedic pedicle screw holding and releasing system comprising:
 a longitudinal screw holding means including two opposite longitudinal slots and an internal threading means, an end of the longitudinal screw holding means having an attachment means for holding a pedicle screw, the pedicle screw inserted to the attachment means by an engaging pressure on the pedicle screw in a direction towards the longitudinal screw holding means, and for separating from the pedicle screw by a releasing pressure on the pedicle screw away from the longitudinal screw holding means; and
 a screw release means having an external threading means,
 wherein the internal threading means of the longitudinal screw holding means and the external threading means of the screw release means are configured for threadably engaging with each other to provide the releasing pressure to the pedicle screw by the screw release means.

11. The orthopedic pedicle screw holding and releasing system according to claim 10, wherein the attachment means includes a longitudinal ridge or a longitudinal groove arranged in parallel to a main axis of the longitudinal screw holding means, dimensioned to receive a corresponding longitudinal groove or longitudinal ridge, respectively, of the pedicle screw.

12. The orthopedic pedicle screw holding and releasing system according to claim 10, wherein the longitudinal screw holding means is configured for threadably engaging by the internal threading means with an external threading of a multi-use instrument or a threading of a set screw inside the longitudinal screw holding means.

13. The orthopedic pedicle screw holding and releasing system according to claim 10, wherein the attachment means is configured for guiding the pedicle screw during the insertion to the longitudinal screw holding means along a direction of a main axis of the longitudinal screw holding means.

14. The orthopedic pedicle screw holding and releasing system according to claim 10, wherein the longitudinal screw holding means is made of one piece of elastic material.

15. The orthopedic pedicle screw holding and releasing system according to claim 10, wherein the attachment means is configured such that the releasing pressure on the pedicle screw by the screw release means progressively separates the pedicle screw from the longitudinal screw holding means.

16. The orthopedic pedicle screw holding and releasing system according to claim 10, wherein the attachment means is configured such that the releasing pressure on the pedicle screw by the screw release means progressively separates the pedicle screw from the longitudinal screw holding means without laterally expanding the longitudinal screw holding means.

17. The orthopedic pedicle screw holding and releasing system according to claim 10, wherein the two opposite longitudinal slots include an open end towards the end of the longitudinal screw holding means.

18. An implant kit having the orthopedic pedicle screw holding and releasing system according to claim 10.

* * * * *